(12) United States Patent
Allon et al.

(10) Patent No.: US 8,603,819 B2
(45) Date of Patent: Dec. 10, 2013

(54) COMPOSITIONS AND METHODS FOR GENERATING MUSCULOSKELETAL TISSUE

(75) Inventors: Aliza Apple Allon, San Francisco, CA (US); Jeffrey Charles Lotz, San Mateo, CA (US); Richard Alan Schneider, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 190 days.

(21) Appl. No.: 12/993,668

(22) PCT Filed: May 22, 2009

(86) PCT No.: PCT/US2009/003189

§ 371 (c)(1),
(2), (4) Date: Apr. 7, 2011

(87) PCT Pub. No.: WO2009/142770

PCT Pub. Date: Nov. 26, 2009

(65) Prior Publication Data

US 2011/0177132 A1    Jul. 21, 2011

Related U.S. Application Data

(60) Provisional application No. 61/055,834, filed on May 23, 2008.

(51) Int. Cl.
*C12N 5/07* (2010.01)
(52) U.S. Cl.
USPC ........... 435/393; 435/177; 435/382; 435/375; 424/93.7
(58) Field of Classification Search
None
See application file for complete search history.

(56) References Cited

U.S. PATENT DOCUMENTS

| | | | |
|---|---|---|---|
| 5,486,359 A | 1/1996 | Caplan et al. | |
| 5,723,331 A * | 3/1998 | Tubo et al. | 435/366 |
| 5,908,784 A | 6/1999 | Johnstone et al. | |
| 6,355,239 B1 | 3/2002 | Bruder et al. | |
| 6,835,377 B2 | 12/2004 | Goldberg et al. | |
| 2005/0069572 A1 | 3/2005 | Williams et al. | |
| 2007/0292514 A1 | 12/2007 | Chan Pui et al. | |

FOREIGN PATENT DOCUMENTS

WO    WO 03/068149    8/2003

OTHER PUBLICATIONS

Le Visage et al., "Interaction of Human Mesenchymal Stem Cells With Disc Cells", (2006) *Spine*, 31(18):2036-2042.
Richardson et al., "Intervertebral Disc Cell-Mediated Mesenchymal Stem Cell Differentiation", (2006) *Stem Cells*, 24:707-716.
Vadalá et al., "Coculture of Bone Marrow Mesenchymal Stem Cells and Nucleus Pulposus Cells Modulate Gene Expression Profile Without Cell Fusion", (2008) *Spine*, 33(8):870-876.
Yamamoto et al., "Upregulation of the Viability of Nucleus Pulposus Cells by Bone Marrow-Derived Stromal Cells", (2004) *Spine*, 29(14):1508-1514.

* cited by examiner

*Primary Examiner* — Allison Ford
(74) *Attorney, Agent, or Firm* — Paula A. Borden; Bozicevic, Field & Francis LLP

(57) ABSTRACT

The present disclosure provides compositions comprising musculoskeletal cells and mesenchymal stem cells in discrete regions. The present disclosure provides systems comprising a subject composition; and methods of using a subject composition to generate cartilage, bone, tendon, muscle, intervertebral disc, or other musculoskeletal tissues.

47 Claims, 9 Drawing Sheets

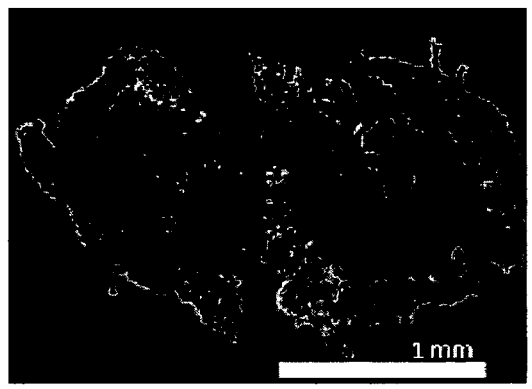 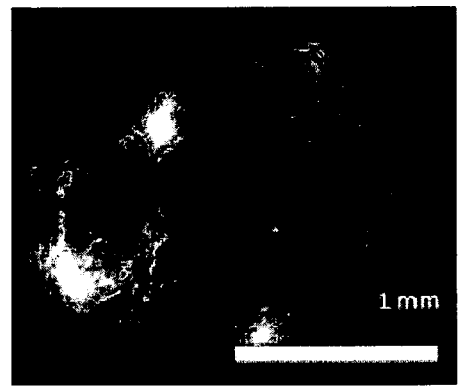
*FIG. 3A*          *FIG. 3B*
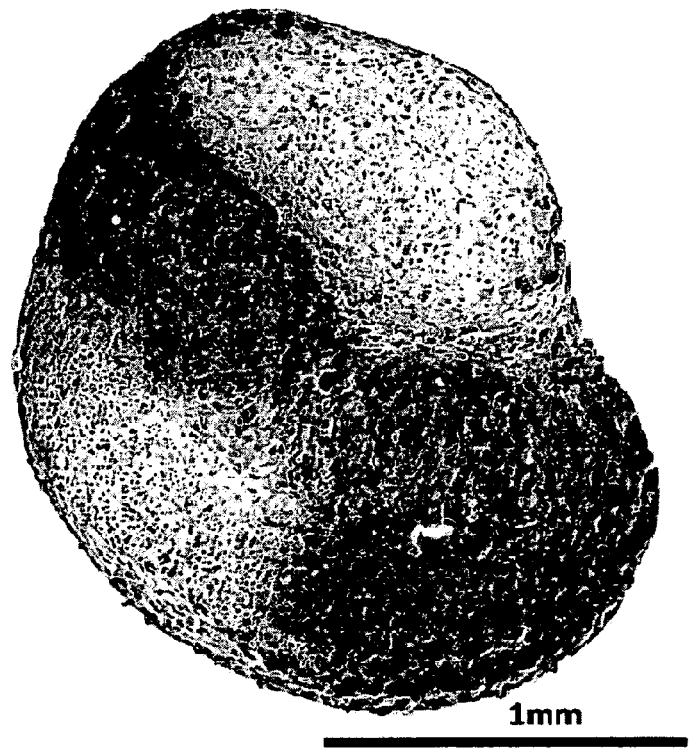
*FIG. 4*

0.5mm 0.25mm

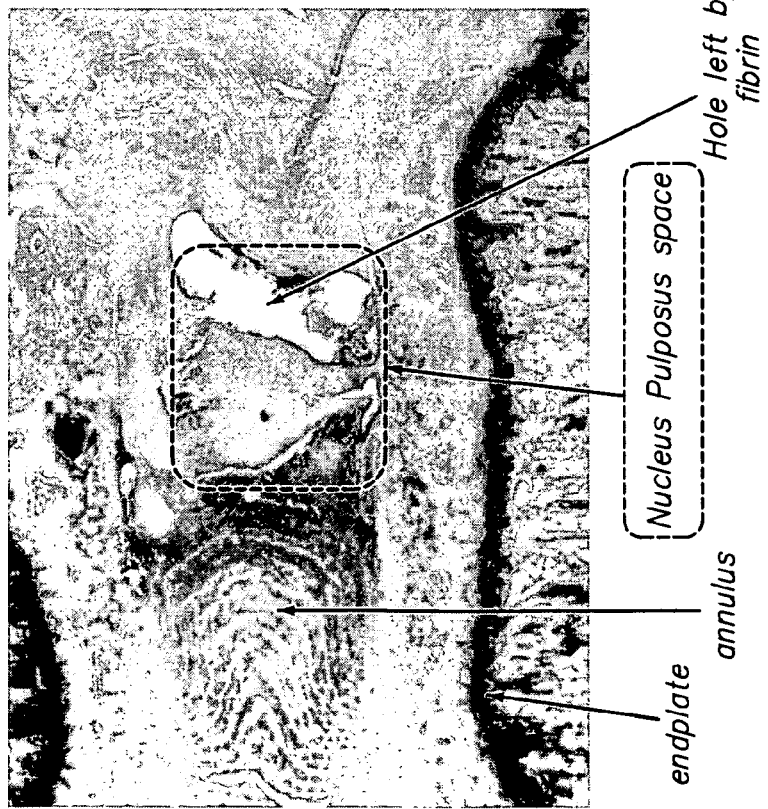
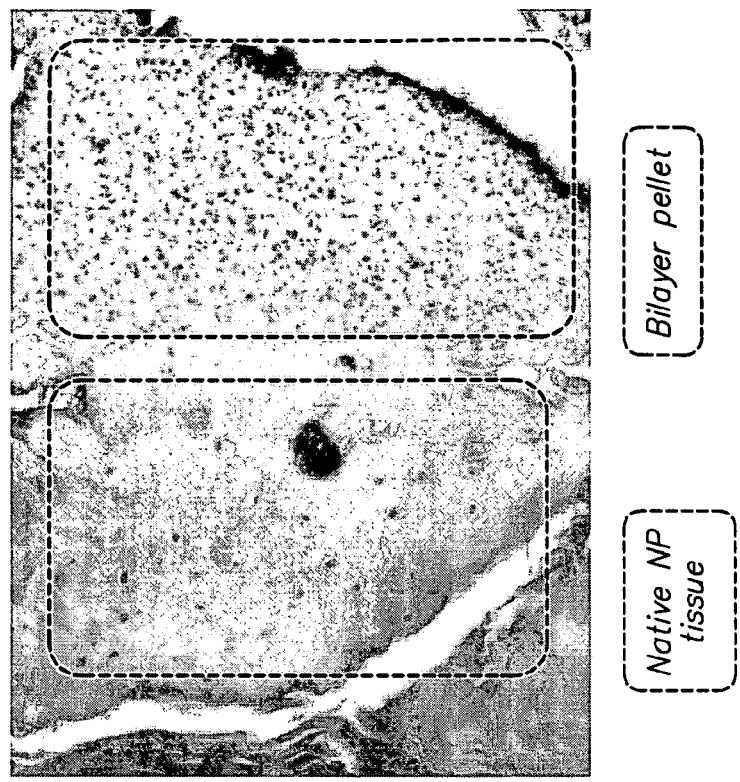
FIG. 10B
FIG. 10A

COMPOSITIONS AND METHODS FOR GENERATING MUSCULOSKELETAL TISSUE

CROSS-REFERENCE

This application claims the benefit of U.S. Provisional Patent Application No. 61/055,834, filed May 23, 2008, which application is incorporated herein by reference in its entirety.

STATEMENT REGARDING FEDERALLY SPONSORED RESEARCH

This invention was made with government support under AR049786 awarded by the National Institutes of Health. The government has certain rights in the invention.

BACKGROUND

The musculoskeletal system includes a variety of dense and soft connective tissues, including cartilage, bone, tendon, ligament, spinal intervertebral discs, and muscle. Musculoskeletal tissues differentiate embryonically from mesenchymal precursor cells.

An example of musculoskeletal tissue is cartilage. Three types of cartilage exist in mammals: hyaline cartilage, fibrocartilage, and elastic cartilage. Hyaline cartilage includes the articular cartilage of the joints, the cartilages of the trachea, bronchi, and larynx, and the nasal cartilages. Fibrocartilage is found in the intervertebral disc, tendinous and ligamentous insertions, menisci, the symphysis pubis, and insertions of joint capsules. Elastic cartilage is found in the pinna of the ears, in the epiglottis, and in the arytenoid cartilages of the larynx.

Musculoskeletal tissues play a variety of functional roles. For example, the spinal intervertebral discs serve as the shock absorbers of the axial body and also allow for considerable flexibility and motion. Each disc is composed of a peripheral, ligament-like annulus fibrosus and a central nucleus pulposus (NP). The NP contains chondrocyte-like cells embedded in a matrix of proteoglycan and type II collagen that is highly hydrophilic and allows the tissue to swell to resist compressive forces. The NP environment is one of high pressure, low pH, and low oxygen tension.

Musculoskeletal diseases are a major health concern. As an example, disc degeneration is a common feature among the aging population and is the underlying cause of various spinal disorders and disabilities. Disc degeneration is also believed to be the predominant cause of low back pain, which is the second most frequent reason for patients to visit their physicians and affects approximately 80% of the population at some point in their lives. When patients fail to respond to conservative care, a spinal fusion is typically performed even though it leads to immobility of the treated segments and predisposes adjacent discs to accelerated degeneration. A significant number of these patients do not benefit from fusion and require further treatments.

Another adverse musculoskeletal condition is arthritis, which affects millions of people in the United States alone. Although metallic joint replacements offer relief for some individuals with advanced disease, these devices have limited durability and are not suitable for young or highly active patients. Focal cartilage defects represent an early manifestation of arthritis. Sports injuries and trauma-induced focal cartilage defects are typically treated with microfracture (a procedure where small holes are drilled thru cartilage and into the underlying bone to stimulate healing), which has short-term benefits but also fails after 5-10 years. Despite its limitations, microfracture remains the gold standard for treatment. Recently, therapies that utilize autologous chondrocytes have been pursued; however, the use of a patient's own articular cartilage cells is critically limited by insufficient cell availability, donor site morbidity, cell heterogeneity, and inconsistent regenerative capacity.

There is a need in the art for compositions and methods of producing various musculoskeletal tissues.

Literature

Richardson et al. (2006) *Stem Cells* 24:707; Yamamoto et al. (2004) *Spine* 29:1508; Le Visage et al. (2006) *Spine* 31:2036; Vadalá et al. (2008) *Spine* 33:870; WO 2003/068149; U.S. Pat. Nos. 6,355,239, 5,908,784, 5,486,359, 6,835,377.

SUMMARY OF THE INVENTION

The present disclosure provides compositions comprising musculoskeletal cells and mesenchymal stem cells in discrete regions. The present disclosure provides systems comprising a subject composition; and methods of using a subject composition to generate cartilage, bone, tendon, muscle, intervertebral disc, or other musculoskeletal tissues.

BRIEF DESCRIPTION OF THE DRAWINGS

FIGS. 3A and 3B depict frozen sections of bilaminar pellets after 3 weeks in in vitro culture.

FIG. 4 depicts a three-week bilaminar pellet (cell composition) with mesenchymal stem cells (MSC) on the inside (inner layer) and nucleus pulposus cells (NPC) on the outside (outer layer) after undergoing budding and satellite pellet formation.

FIGS. 10A and 10B depict histological analysis of a rat disc 2 weeks after introduction of a bilayer cell composition.

DEFINITIONS

Figure 1:
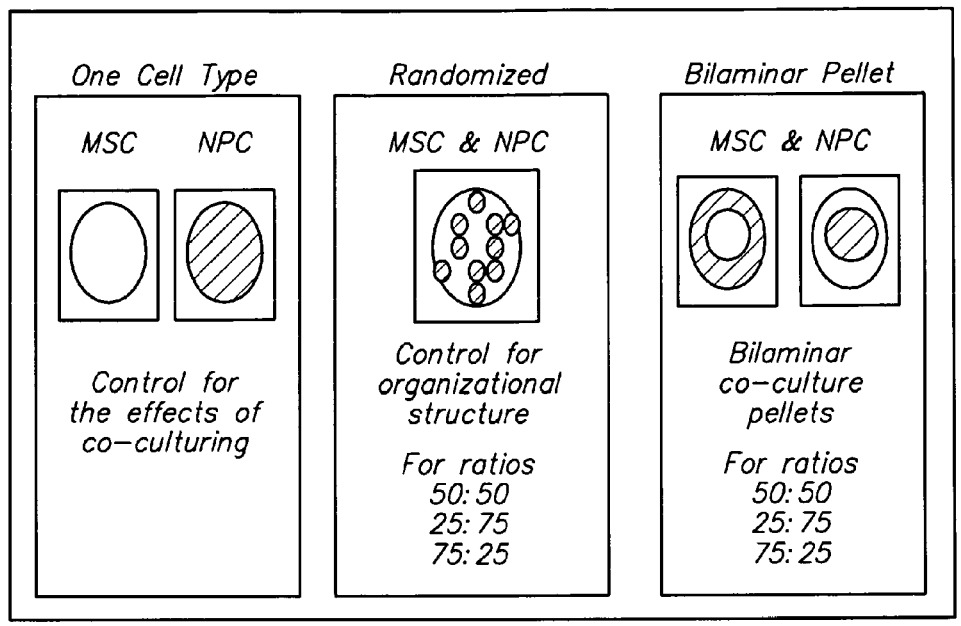
FIG. 1 is a schematic depiction of the experimental cell groups.
Figures 2A, 2B, 2C, 2D:
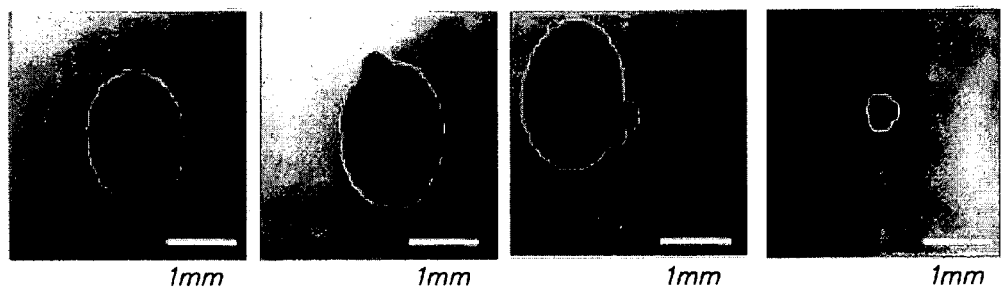
FIGS. 2A-D depict formation of satellite ("progeny") cell compositions after various times in in vitro culture.

The term "chondrocyte" refers to a cartilage-specific cell that gives rise to normal cartilage tissue growth in vivo; chondrocytes synthesize and deposit the supportive matrix (composed principally of collagen and proteoglycan) of cartilage.

As used herein, the term "mesenchymal stem cell" ("MSC"), both in singular and plural forms, refers to a stem cell that is capable of differentiating into more than one specific type of mesenchymal tissue cell. MSC can differentiate into the various mesenchymal lineages, for example, chondrocytes, myocytes, osteocytes, and tenocytes, as well as precursors of these cells, e.g., chondroblasts, myoblasts, and osteoblasts. MSC may express one or more cell surface markers, such as bone morphogenetic protein receptor (BMPR), STRO-1, CD105, CD166, CD29, and CD44. MSC are generally CD34 negative (CD34$^-$). MSC can be positive for CD105, CD166, CD29, and CD44; and negative for CD14, CD34 and CD45.

The term "induced pluripotent stem cell" (or "iPS cell"), as used herein, refers to a pluripotent stem cell induced from a somatic cell, e.g., a differentiated somatic cell. iPS cells are capable of self-renewal and differentiation into cell fate-committed stem cells, including mesencymal stem cells, as well as various types of mature cells such as chondrocytes, osteocytes, etc.

The term "cross-linked" as used herein refers to a composition containing intermolecular cross-links and/or intramolecular cross-links arising from the formation of covalent bonds, ionic bonds, hydrogen bonding, or any combination thereof "Cross-linkable" refers to a component or compound that is capable of undergoing reaction to form a cross-linked composition.

The terms "biocompatible polymer", "biocompatible cross-linked polymer matrix" and "biocompatibility" when used in relation to polymers are art-recognized terms. For example, biocompatible polymers include polymers that are neither themselves toxic to the host (e.g., a non-human animal or a human), nor degrade (if the polymer degrades) at a rate that produces monomeric or oligomeric subunits or other byproducts at toxic concentrations in the host. In certain embodiments, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer.

A "biocompatible" carrier or other component is a carrier or other component that does not substantially induce an undesirable response in an individual, e.g., the carrier or other component does not substantially induce an immune response in the host, does not substantially induce an inflammatory response in the host, etc.

"Injectable" as used herein means capable of being administered, delivered, or carried into the body via syringes, catheters, needles, and other means for injecting or infusing a composition in a liquid medium.

The terms "subject," "individual," "host," and "patient" are used interchangeably herein to refer to a member or members of any mammalian species. Individuals thus include, without limitation, humans, non-human primates, canines, felines, ungulates (e.g., equine (e.g., horses), bovine (e.g., cows), swine (e.g., pig), camels, etc.), rodents (e.g., rats, mice), and other mammalian subjects. Non-human animal models, particularly mammals, e.g. a non-human primate, a murine (e.g., a mouse, a rat), lagomorpha, etc. may be used for experimental investigations.

"Treating" or "treatment" of a condition, disorder, or disease includes: (1) preventing at least one symptom of the condition, disorder, or disease, e.g., causing a clinical symptom to not significantly develop in a mammal that may be exposed to or predisposed to a disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammalian subject for the treatment of a condition, disorder, or disease, is sufficient, in combination with another agent, or alone in one or more doses, to effect such treatment for the condition, disorder, or disease. The "therapeutically effective amount" will vary depending on the compound, the condition, disorder, or disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a mesenchymal stem cell" includes a plurality of such cells and reference to "the chondrogenic factor" includes reference to one or more chondrogenic factors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions comprising musculoskeletal cells and mesenchymal stem cells in discrete regions. The present disclosure provides systems comprising a subject composition; and methods of using a subject composition to generate cartilage, bone, tendon, muscle, intervertebral disc, or other musculoskeletal tissues.

The inventors have found that a structured, three-dimensional co-culture system that includes a dense population of immature, naïve cells such as mesenchymal stem cells within a layer of more mature, instructive cells (e.g., chondrocytes) provides a configuration that maximizes surface area to volume and enables important inductive cell-cell interactions that efficiently self-promote differentiation of the immature cells, thereby reducing or eliminating the need for exogenous differentiation factors.

The present disclosure provides a multi-layer three-dimensional cell composition comprising a less differentiated ("naïve" or "immature") cell and a more differentiated ("instructive" or "mature") cell. The present disclosure provides a multi-layer cell composition comprising a chondroblast, a chondrocyte, an osteoblast, an osteocyte, a myoblast, a myocyte, a tenocyte, or a nucleus pulposus cell; and a stem cell or progenitor cell, e.g., a mesenchymal stem cell (MSC). The present disclosure further provides compositions comprising a subject multi-layer cell composition; and a biocompatible carrier. Depending on the cells included in the composition, a subject composition is useful for producing a musculoskeletal tissue such as cartilage, intervertebral disc tissue (e.g., nucleus pulposus tissue), muscle, tendon, or bone. Thus, the present disclosure provides cartilage production compositions, intervertebral disc production compositions, muscle production compositions, tendon production compositions, and bone production compositions.

A number of conditions and disorders can be treated by providing a cell composition that produces cartilage. Conditions and disorders that can be treated by providing a cell composition that produces cartilage are discussed in more detail below, and include disorders ranging from chronic degeneration brought about by disease, overuse, or trauma, to plastic or reconstructive surgery. As such, the present invention provides methods of generating cartilage, including in vivo methods of generating cartilage, where the methods generally involve introducing into an individual in need of cartilage replacement and/or cartilage regeneration an effective amount of a subject cell composition.

Various conditions and disorders can be treated by providing a cell composition that produces bone or bone components. Conditions and disorders that can be treated by providing a bone production composition include bone trauma (e.g., fractures, and the like); and degenerative bone disorders.

Multi-Layer Cell Compositions

The present disclosure provides a multi-layer cell composition in which more differentiated cells and less differentiated cells are co-cultured in a multi-layer, three-dimensional configuration that mimics normal development.

A subject multi-layer three-dimensional cell composition includes: 1) a first layer comprising a first, more differentiated, cell type; and 2) a second layer comprising a second, less differentiated, cell type. The first and second layers form discrete regions in a composition, e.g., the first layer (e.g., first discrete region) includes cells in which the cells are at least 85% of a first, more differentiated, cell type, and the second layer (e.g., second discrete region) includes cells in which the cells are at least 85% of a second, less differentiated, cell type. The layers are not monolayers, e.g., the layers are at least two cells thick, e.g., at least 2-5 cells thick, at least 5-10 cells thick, at least 10-50 cells thick, or more than 50 cells thick. In other words, a subject multi-layer cell composition has a three-dimensional configuration.

A subject multi-layer cell composition includes a first layer comprising a first, more differentiated ("instructive"), cell type. Suitable more differentiated cells include, e.g., osteoblasts, osteocytes, chondroblasts, chondrocytes, myoblasts, myocytes, tenocytes, and nucleus pulposus cells (NPC). A subject multi-layer cell composition includes a second layer comprising a second, less differentiated ("naïve"), cell type. Suitable less differentiated cell types include stem cells (e.g., adult stem cells, embryonic stem cells, and induced pluripotent stem (iPS) cells); and mesenchymal stem cells (MSC). In some instances, the layer comprising the less differentiated cell type is surrounded (partially or substantially completely) by the layer comprising the more differentiated cell type. In some instances, the layer comprising the more differentiated cell type is surrounded (partially or substantially completely) by the layer comprising the less differentiated cell type.

A "more differentiated" cell of a subject multi-cell layer does not include a fibroblast. Thus, e.g., the cells of a layer of a subject multi-layer cell composition generally comprise less than about 15%, less than about 10%, less than about 5%, less than about 2%, or less than about 1% fibroblasts.

In some instances, a subject cell composition has only two layers, e.g., a first layer comprising a first, more differentiated cell type and a second layer comprising a second, less differentiated cell type. Such a two-layer cell composition (also referred to herein as a "bilaminar cell composition") can include one or more additional components (e.g., a buffer, one or more chondrogenic factors, one or more osteogenic factors, a scaffold component, etc.), as described in detail below. In some instances, the layer comprising the less differentiated cell type is surrounded (partially or substantially completely) by the layer comprising the more differentiated cell type. In some instances, the layer comprising the more differentiated cell type is surrounded (partially or substantially completely) by the layer comprising the less differentiated cell type.

The more differentiated cells and the less differentiated cells are present in a subject cell composition at a ratio of 1:1 or greater than 1:1. For example, the ratio of more differentiated cells to less differentiated cells in a subject multi-layer cell composition is at least about 1:1, at least about 1.5:1, at least about 2:1, at least about 2.5:1, at least about 3:1, at least about 3.5:1, at least about 4:1, at least about 4.5:1, at least about 5:1, at least about 5.5:1, at least about 6:1, at least about 7:1, at least about 8:1, at least about 9:1, or at least about 10:1. For example, the ratio of more differentiated cells to less differentiated cells in a subject multi-layer cell composition can range from about 1:1 to about 1.25:1, from about 1.25:1 to about 1.5:1, from about 1.5:1 to about 2:1, from about 2:1 to about 3:1, from about 3:1 to about 4:1, from about 4:1 to about 5:1, from about 5:1 to about 6:1, from about 6:1 to about 7:1, from about 7:1 to about 8:1, from about 8:1 to about 9:1, or from about 9:1 to about 10:1, or greater than 10:1.

As an example, a subject cell composition can include NPC and mesenchymal stem cells (MSC). NPC and MSC can be present in a subject cell composition at a ratio of 1:1 or greater than 1:1. For example, the ratio of NPC to MSC in a subject composition can be at least about 1:1, at least about 1.5:1, at least about 2:1, at least about 2.5:1, at least about 3:1, at least about 3.5:1, at least about 4:1, at least about 4.5:1, at least about 5:1, at least about 5.5:1, at least about 6:1, at least about 7:1, at least about 8:1, at least about 9:1, or at least about 10:1. For example, the ratio of NPC to MSC in a subject composition can range from about 1:1 to about 1.25:1, from about 1.25:1 to about 1.5:1, from about 1.5:1 to about 2:1, from about 2:1 to about 3:1, from about 3:1 to about 4:1, from about 4:1 to about 5:1, from about 5:1 to about 6:1, from about 6:1 to about 7:1, from about 7:1 to about 8:1, from about 8:1 to about 9:1, or from about 9:1 to about 10:1, or greater than 10:1.

As another example, a subject cell composition can include osteocytes (or osteoblasts, or a mixture of osteocytes and osteoblasts) and MSC. Osteocytes (or osteoblasts, or a mixture of osteocytes and osteoblasts) and MSC can be present in a subject cell composition at a ratio of 1:1 or greater than 1:1. For example, the ratio of osteocytes (or osteoblasts, or a mixture of osteocytes and osteoblasts) to MSC in a subject composition can be at least about 1:1, at least about 1.5:1, at least about 2:1, at least about 2.5:1, at least about 3:1, at least about 3.5:1, at least about 4:1, at least about 4.5:1, at least about 5:1, at least about 5.5:1, at least about 6:1, at least about 7:1, at least about 8:1, at least about 9:1, or at least about 10:1. For example, the ratio of osteocytes (or osteoblasts, or a mixture of osteocytes and osteoblasts) to MSC in a subject composition can range from about 1:1 to about 1.25:1, from about 1.25:1 to about 1.5:1, from about 1.5:1 to about 2:1, from about 2:1 to about 3:1, from about 3:1 to about 4:1, from about 4:1 to about 5:1, from about 5:1 to about 6:1, from about 6:1 to about 7:1, from about 7:1 to about 8:1, from about 8:1 to about 9:1, or from about 9:1 to about 10:1, or greater than 10:1.

As an example, a subject cell composition can include chondrocytes (or chondroblasts, or a mixture of chondrocytes and chondroblasts) and MSC. Chondrocytes (or chondroblasts, or a mixture of chondrocytes and chondroblasts) and MSC can be present in a subject cell composition at a ratio of 1:1 or greater than 1:1. For example, the ratio of chondrocytes (or chondroblasts, or a mixture of chondrocytes and chondroblasts) to MSC in a subject composition can be at least about 1:1, at least about 1.5:1, at least about 2:1, at least about 2.5:1, at least about 3:1, at least about 3.5:1, at least about 4:1, at least about 4.5:1, at least about 5:1, at least about 5.5:1, at least about 6:1, at least about 7:1, at least about 8:1, at least about 9:1, or at least about 10:1. For example, the ratio of chondrocytes (or chondroblasts, or a mixture of chondrocytes and chondroblasts) to MSC in a subject composition can range from about 1:1 to about 1.25:1, from about 1.25:1 to about 1.5:1, from about 1.5:1 to about 2:1, from about 2:1 to about 3:1, from about 3:1 to about 4:1, from about 4:1 to about 5:1, from about 5:1 to about 6:1, from about 6:1 to about 7:1, from about 7:1 to about 8:1, from about 8:1 to about 9:1, or from about 9:1 to about 10:1, or greater than 10:1.

As an example, a subject cell composition can include myocytes (or myoblasts, or a mixture of myocytes and myoblasts) and MSC. Myocytes (or myoblasts, or a mixture of myocytes and myoblasts) and MSC can be present in a subject cell composition at a ratio of 1:1 or greater than 1:1. For example, the ratio of myocytes (or myoblasts, or a mixture of myocytes and myoblasts) to MSC in a subject composition can be at least about 1:1, at least about 1.5:1, at least about 2:1, at least about 2.5:1, at least about 3:1, at least about 3.5:1, at least about 4:1, at least about 4.5:1, at least about 5:1, at least about 5.5:1, at least about 6:1, at least about 7:1, at least about 8:1, at least about 9:1, or at least about 10:1. For example, the ratio of myocytes (or myoblasts) to MSC in a subject composition can range from about 1:1 to about 1.25:1, from about 1.25:1 to about 1.5:1, from about 1.5:1 to about 2:1, from about 2:1 to about 3:1, from about 3:1 to about 4:1, from about 4:1 to about 5:1, from about 5:1 to about 6:1, from about 6:1 to about 7:1, from about 7:1 to about 8:1, from about 8:1 to about 9:1, or from about 9:1 to about 10:1, or greater than 10:1.

In some instances, the less differentiated cells and the more differentiated cells are present in a subject cell composition at a ratio of 1:1 or greater than 1:1. For example, the ratio of less differentiated cells to more differentiated cells in a subject multi-layer cell composition is at least about 1:1, at least about 1.5:1, at least about 2:1, at least about 2.5:1, at least about 3:1, at least about 3.5:1, at least about 4:1, at least about 4.5:1, at least about 5:1, at least about 5.5:1, at least about 6:1, at least about 7:1, at least about 8:1, at least about 9:1, or at least about 10:1. For example, the ratio of less differentiated cells to more differentiated cells in a subject multi-layer cell composition can range from about 1:1 to about 1.25:1, from about 1.25:1 to about 1.5:1, from about 1.5:1 to about 2:1, from about 2:1 to about 3:1, from about 3:1 to about 4:1, from about 4:1 to about 5:1, from about 5:1 to about 6:1, from about 6:1 to about 7:1, from about 7:1 to about 8:1, from about 8:1 to about 9:1, or from about 9:1 to about 10:1, or greater than 10:1.

As an example, a subject cell composition can include MSC and NPC, where MSC and NPC are present in a subject cell composition at a ratio of 1:1 or greater than 1:1. For example, the ratio of MSC to NPC in a subject composition is at least about 1:1, at least about 1.5:1, at least about 2:1, at least about 2.5:1, at least about 3:1, at least about 3.5:1, at least about 4:1, at least about 4.5:1, at least about 5:1, at least about 5.5:1, at least about 6:1, at least about 7:1, at least about 8:1, at least about 9:1, or at least about 10:1. For example, the ratio of MSC to NPC in a subject composition can range from about 1:1 to about 1.25:1, from about 1.25:1 to about 1.5:1, from about 1.5:1 to about 2:1, from about 2:1 to about 3:1, from about 3:1 to about 4:1, from about 4:1 to about 5:1, from about 5:1 to about 6:1, from about 6:1 to about 7:1, from about 7:1 to about 8:1, from about 8:1 to about 9:1, or from about 9:1 to about 10:1, or greater than 10:1.

As another example, a subject cell composition can include MSC and osteocytes or osteoblasts, where the MSC and the osteocytes (or osteoblasts, or a mixture of osteocytes and osteoblasts) are present in a subject cell composition at a ratio of 1:1 or greater than 1:1. For example, the ratio of MSC to osteocytes (or osteoblasts, or a mixture of osteocytes and osteoblasts) in a subject composition is at least about 1:1, at least about 1.5:1, at least about 2:1, at least about 2.5:1, at least about 3:1, at least about 3.5:1, at least about 4:1, at least about 4.5:1, at least about 5:1, at least about 5.5:1, at least about 6:1, at least about 7:1, at least about 8:1, at least about 9:1, or at least about 10:1. For example, the ratio of MSC to osteocytes (or osteoblasts, or a mixture of osteocytes and osteoblasts) in a subject composition can range from about 1:1 to about 1.25:1, from about 1.25:1 to about 1.5:1, from about 1.5:1 to about 2:1, from about 2:1 to about 3:1, from about 3:1 to about 4:1, from about 4:1 to about 5:1, from about 5:1 to about 6:1, from about 6:1 to about 7:1, from about 7:1 to about 8:1, from about 8:1 to about 9:1, or from about 9:1 to about 10:1, or greater than 10:1.

As another example, a subject cell composition can include MSC and chondrocytes (or chondroblasts, or a mixture of chondrocytes and chondroblasts) where the MSC and the chondrocytes (or chondroblasts, or a mixture of chondrocytes and chondroblasts) are present in a subject cell composition at a ratio of 1:1 or greater than 1:1. For example, the ratio of MSC to chondrocytes (or chondroblasts, or a mixture of chondrocytes and chondroblasts) in a subject composition is at least about 1:1, at least about 1.5:1, at least about 2:1, at least about 2.5:1, at least about 3:1, at least about 3.5:1, at least about 4:1, at least about 4.5:1, at least about 5:1, at least about 5.5:1, at least about 6:1, at least about 7:1, at least about 8:1, at least about 9:1, or at least about 10:1. For example, the ratio of MSC to chondrocytes (or chondroblasts, or a mixture of chondrocytes and chondroblasts) in a subject composition can range from about 1:1 to about 1.25:1, from about 1.25:1 to about 1.5:1, from about 1.5:1 to about 2:1, from about 2:1 to about 3:1, from about 3:1 to about 4:1, from about 4:1 to about 5:1, from about 5:1 to about 6:1, from about 6:1 to about 7:1, from about 7:1 to about 8:1, from about 8:1 to about 9:1, or from about 9:1 to about 10:1, or greater than 10:1.

As another example, a subject cell composition can include MSC and myocytes (or myoblasts, or a mixture of myocytes and myoblasts) where the MSC and the myocytes (or myoblasts, or a mixture of myocytes and myoblasts) are present in a subject cell composition at a ratio of 1:1 or greater than 1:1. For example, the ratio of MSC to myocytes (or myoblasts, or a mixture of myocytes and myoblasts) in a subject composition is at least about 1:1, at least about 1.5:1, at least about 2:1, at least about 2.5:1, at least about 3:1, at least about 3.5:1, at least about 4:1, at least about 4.5:1, at least about 5:1, at least about 5.5:1, at least about 6:1, at least about 7:1, at least about 8:1, at least about 9:1, or at least about 10:1. For example, the ratio of MSC to myocytes (or myoblasts, or a mixture of myocytes and myoblasts) in a subject composition can range from about 1:1 to about 1.25:1, from about 1.25:1 to about 1.5:1, from about 1.5:1 to about 2:1, from about 2:1 to about 3:1, from about 3:1 to about 4:1, from about 4:1 to about 5:1, from about 5:1 to about 6:1, from about 6:1 to about 7:1, from about 7:1 about 8:1, from about 8:1 to about 9:1, or from about 9:1 to about 10:1, or greater than 10:1.

The spatial relationship between the more differentiated cells (e.g., chondroblasts, chondrocytes, osteoblasts, osteocytes, myoblasts, myocytes, tenocytes, or NPC) and the less differentiated cells (e.g., adult stem cells, embryonic stem cells, iPS cells, MSC, etc.) is non-random, e.g., a subject composition is not a randomly distributed mixture of more differentiated cells and less differentiated cells. Instead, a subject composition comprises a first layer (e.g., a first discrete region) comprising a plurality of more differentiated cells (e.g., chondroblasts, chondrocytes, osteoblasts, osteocytes, myoblasts, myocytes, tenocytes, or NPC); and a second layer (e.g., a second discrete region) comprising a plurality of less differentiated cells (e.g., adult stem cells, embryonic stem cells, iPS cells, MSC, etc.).

The cells in the first layer are at least about 85%, at least about 90%, at least about 95%, or greater than 95%, of a single, more differentiated, cell type (e.g., chondroblasts, chondrocytes, osteoblasts, osteocytes, myoblasts, myocytes, tenocytes, or NPC). The cells in the second layer are at least about 85%, at least about 90%, at least about 95%, or greater than 95%, of a single, less differentiated, cell type (e.g., adult stem cells, embryonic stem cells, iPS cells, MSC, etc.).

As an example, the cells in the first layer are at least about 85% NPC, at least about 90% NPC, at least about 95% NPC, or greater than 95% NPC; and the cells in the second layer are at least about 85% MSC, at least about 90% MSC, at least about 95% MSC, or greater than 95% MSC. As another example, the cells in the first layer are at least about 85% osteocytes or osteoblasts, at least about 90% osteocytes (or osteoblasts), at least about 95% osteocytes (or osteoblasts), or greater than 95% osteocytes (or osteoblasts); and the cells in the second layer are at least about 85% MSC, at least about 90% MSC, at least about 95% MSC, or greater than 95% MSC. As another example, the cells in the first layer are at least about 85% chondrocytes or chondroblasts, at least about 90% chondrocytes (or chondroblasts), at least about 95% chondrocytes (or chondroblasts), or greater than 95% chondrocytes (or chondroblasts); and the cells in the second layer are at least about 85% MSC, at least about 90% MSC, at least about 95% MSC, or greater than 95% MSC. As another example, the cells in the first layer are at least about 85% myocytes or myoblasts, at least about 90% myocytes (or myoblasts), at least about 95% myocytes (or myoblasts), or greater than 95% myocytes (or myoblasts); and the cells in the second layer are at least about 85% MSC, at least about 90% MSC, at least about 95% MSC, or greater than 95% MSC. As another example, the cells in the first layer are at least about 85% tenocytes, at least about 90% tenocytes, at least about 95% tenocytes, or greater than 95% tenocytes; and the cells in the second layer are at least about 85% MSC, at least about 90% MSC, at least about 95% MSC, or greater than 95% MSC.

The first layer and the second layer can have any of a variety of spatial relationships. For example, the first layer can completely surround the second layer. As another example, the first layer can incompletely (e.g., partially) surround the second layer. As another example, the first layer and the second layer can have a side-by-side spatial relationship. Other spatial relationships are possible. In some embodiments, a subject multi-layer cell composition has a roughly spherical form, in which the more differentiated cells are present in an inner layer and the less differentiated cells are present in an outer layer. In other embodiments, a subject multi-layer cell composition has a roughly spherical form, in which the less differentiated cells are present in an inner layer and the more differentiated cells are present in an outer layer.

As an example, a subject composition can comprise NPC and MSC in a substantially spherical form, in which the NPC are in a first layer, the MSC are in a second layer, and in which the second layer surrounds the first layer, e.g., the first layer is an inner layer and the second layer is an outer layer. As an example, a subject composition can comprise NPC and MSC in a spherical form, in which the NPC are in a first layer, the MSC are in a second layer, and in which the second layer surrounds the first layer, e.g., the second layer is an inner layer and the first layer is an outer layer. As other examples, a subject cell composition can comprise NPC and MSC in a cuboidal form, in a cylindrical form, in a rectangular prism form, or in an irregular form.

As another example, a subject composition can comprise NPC and MSC in a substantially spherical form, in which the MSC are in a first layer, the NPC are in a second layer, and in which the second layer surrounds the first layer, e.g., the first layer is an inner layer and the second layer is an outer layer. As other examples, a subject cell composition can comprise MSC and NPC in a cuboidal form, in a cylindrical form, in a rectangular prism form, or in an irregular form; in some instances, the MSC will be in a first, inner region or layer, and the NPC will be in a second, outer layer or region, and the second layer or region will substantially surround the first layer or region.

As another example, a subject composition can comprise chondrocytes (or chondroblasts) and MSC in a substantially spherical form, in which the MSC are in a first layer, the chondrocytes (or chondroblasts) are in a second layer, and in which the second layer surrounds the first layer, e.g., the first layer is an inner layer and the second layer is an outer layer. As other examples, a subject cell composition can comprise MSC and chondrocytes (or chondroblasts) in a cuboidal form, in a cylindrical form, in a rectangular prism form, or in an irregular form; in some instances, the MSC will be in a first, inner region or layer, and the chondrocytes (or chondroblasts) will be in a second, outer layer or region, and the second layer or region will substantially surround the first layer or region.

As another example, a subject composition can comprise osteocytes (or osteoblasts) and MSC in a substantially spherical form, in which the MSC are in a first layer, the osteocytes (or osteoblasts) are in a second layer, and in which the second layer surrounds the first layer, e.g., the first layer is an inner layer and the second layer is an outer layer. As other examples, a subject cell composition can comprise MSC and osteocytes (or osteoblasts) in a cuboidal form, in a cylindrical form, in a rectangular prism form, or in an irregular form; in some instances, the MSC will be in a first, inner region or layer, and the osteocytes (or osteoblasts) will be in a second, outer layer or region, and the second layer or region will substantially surround the first layer or region.

As another example, a subject composition can comprise myocytes (or myoblasts) and MSC in a substantially spherical form, in which the MSC are in a first layer, the myocytes (or myoblasts) are in a second layer, and in which the second layer surrounds the first layer, e.g., the first layer is an inner layer and the second layer is an outer layer. As other examples, a subject cell composition can comprise MSC and myocytes (or myoblasts) in a cuboidal form, in a cylindrical form, in a rectangular prism form, or in an irregular form; in some instances, the MSC will be in a first, inner region or layer, and the myocytes (or myoblasts) will be in a second, outer layer or region, and the second layer or region will substantially surround the first layer or region.

The dimensions of a subject multi-layer cell composition can vary. For example, where a subject cell composition is substantially spherical, the average diameter of the cell composition can range from about 0.1 mm to about 5 mm, e.g., from about 0.1 mm to about 0.5 mm, from about 0.5 mm to about 0.75 mm, from about 0.75 mm to about 1.0 mm, from about 1.0 mm to about 1.5 mm, from about 1.5 mm to about 2 mm, from about 2 mm to about 3 mm, from about 3 mm to about 4 mm, or from about 4 mm to about 5 mm. Suitable dimensions can depend on a variety of factors, including, e.g., the site of in vivo use.

In some embodiments, a subject multi-layer cell composition has a unit volume of from about 0.05 $mm^3$ to about 0.5 $cm^3$, or more, e.g., from about 0.05 $mm^3$ to about 0.1 $mm^3$, from about 0.1 $mm^3$ to about 0.5 $mm^3$, from about 0.5 $mm^3$ to about 0.75 $mm^3$, from about 0.75 $mm^3$ to about 1.0 $mm^3$, from about 1.0 $mm^3$ to 1.5 $mm^3$, from about 1.5 $mm^3$ to about 2 $mm^3$, from about 2 $mm^3$ to about 3 $mm^3$, from about 3 $mm^3$ to about 4 $mm^3$, from about 4 $mm^3$ to about 5 $mm^3$, from about 5 $mm^3$ to about 7 $mm^3$, from about 7 $mm^3$ to about 8 $mm^3$, or from about 8 $mm^3$ to about 10 $mm^3$, from about 10 $mm^3$ to about 12 $mm^3$, from about 12 $mm^3$ to about 14 $mm^3$, or from about 14 $mm^3$ to about 15 $mm^3$, from about 15 $mm^3$ to about 25 $mm^3$, from about 25 $mm^3$ to about 50 $mm^3$, from about 50 $mm^3$ to about 100 $mm^3$, from about 0.1 $cm^3$ to about 0.2 $cm^3$, from about 0.2 $cm^3$ to about 0.3 $cm^3$, from about 0.3 $cm^3$ to about 0.4 $cm^3$, or from about 0.4 $cm^3$ to about 0.5 $cm^3$.

In some embodiments, a subject multi-layer cell composition has a unit volume of from about 0.1 $mm^3$ to about 5 $mm^3$, or more, e.g., from about 0.1 $mm^3$ to about 0.5 $mm^3$, from about 0.5 $mm^3$ to about 0.75 $mm^3$, from about 0.75 $mm^3$ to about 1.0 $mm^3$, from about 1.0 $mm^3$ to 1.5 $mm^3$, from about 1.5 $mm^3$ to about 2 $mm^3$, from about 2 $mm^3$ to about 3 $mm^3$, from about 3 $mm^3$ to about 4 $mm^3$, or from about 4 $mm^3$ to about 5 $mm^3$.

The number of cells in the first layer can range from about $10^7$ to about $10^9$, e.g., the first layer can comprise from about $10^7$ cells to about $5\times10^7$ cells, from about $5\times10^7$ cells to about $10^3$ cells, from about $10^3$ cells to about $5\times10^3$ cells, from about $5\times10^3$ cells to about $10^4$ cells, from about $10^4$ cells to about $5\times10^4$ cells, from about $5\times10^4$ cells to about $10^5$ cells, from about $10^5$ cells to about $5\times10^5$ cells from about $5\times10^5$ cells to about $10^6$ cells, from about $10^6$ cells to about $5\times10^6$ cells, from about $5\times10^6$ cells to about $10^7$ cells, from about $10^7$ cells to about $5\times10^7$ cells, from about $5\times10^7$ cells to about $10^8$ cells, or from about $5\times10^8$ cells to about $10^9$ cells.

The number of cells in the second layer can range from about $10^7$ to about $10^9$, e.g., the second layer can comprise from about $10^7$ cells to about $5\times10^7$ cells, from about $5\times10^7$ cells to about $10^3$ cells, from about $10^3$ cells to about $5\times10^3$ cells, from about $5\times10^3$ cells to about $10^4$ cells, from about $10^4$ cells to about $5\times10^4$ cells, from about $5\times10^4$ cells to about $10^5$ cells, from about $10^5$ cells to about $5\times10^5$ cells from about $5\times10^5$ cells to about $10^6$ cells, from about $10^6$ cells to about $5\times10^6$ cells, from about $5\times10^6$ cells to about $10^7$ cells, from about $10^7$ cells to about $5\times10^7$ cells, from about $5\times10^7$ cells to about $10^8$ cells, or from about $5\times10^8$ cells to about $10^9$ cells.

The density of cells (including less differentiated cells and more differentiated cells) in a subject multi-layer cell composition can range from about $10^4$ cells/$mm^3$ to about $10^9$ cells/$mm^3$, e.g., from about $10^4$ cells/$mm^3$ to about $10^5$ cells/$mm^3$, from about $10^5$ cells/$mm^3$ to about $10^6$ cells/$mm^3$, from about $10^6$ cells/$mm^3$ to about $10^7$ cells/$mm^3$, from about $10^7$ cells/$mm^3$ to about $10^8$ cells/$mm^3$, or from about $10^8$ cells/$mm^3$ to about $10^9$ cells/$mm^3$, or greater than $10^9$ cells/$mm^3$.

In some embodiments, a subject multi-layer cell composition is referred to as a "multi-layer cell unit," where a unit can have a volume of from about 0.05 $mm^3$ to about 0.5 $cm^3$, or more, e.g., from about 0.05 $mm^3$ to about 0.1 $mm^3$, from about 0.1 $mm^3$ to about 0.5 $mm^3$, from about 0.5 $mm^3$ to about 0.75 $mm^3$, from about 0.75 $mm^3$ to about 1.0 $mm^3$, from about 1.0 $mm^3$ to 1.5 $mm^3$, from about 1.5 $mm^3$ to about 2 $mm^3$, from about 2 $mm^3$ to about 3 $mm^3$, from about 3 $mm^3$ to about 4 $mm^3$, from about 4 $mm^3$ to about 5 $mm^3$, from about 5 $mm^3$ to about 7 $mm^3$, from about 7 $mm^3$ to about 8 $mm^3$, or from about 8 $mm^3$ to about 10 $mm^3$, from about 10 $mm^3$ to about 12 $mm^3$, from about 12 $mm^3$ to about 14 $mm^3$, or from about 14 $mm^3$ to about 15 $mm^3$, from about 15 $mm^3$ to about 25 $mm^3$, from about 25 $mm^3$ to about 50 $mm^3$, from about 50 $mm^3$ to about 100 $mm^3$, from about 0.1 $cm^3$ to about 0.2 $cm^3$, from about 0.2 $cm^3$ to about 0.3 $cm^3$, from about 0.3 $cm^3$ to about 0.4 $cm^3$, or from about 0.4 $cm^3$ to about 0.5 $cm^3$; and where a unit can include from $10^2$ to about $10^9$ cells (e.g., total of less differentiated cells plus more differentiated cells), e.g., from about $10^2$ cells to about $5\times10^2$ cells, from about $5\times10^2$ cells to about $10^3$ cells, from about $10^3$ cells to about $5\times10^3$ cells, from about $5\times10^3$ cells to about $10^4$ cells, from about $10^4$ cells to about $5\times10^4$ cells, from about $5\times10^4$ cells to about $10^5$ cells, from about $10^5$ cells to about $5\times10^5$ cells from about $5\times10^5$ cells to about $10^6$ cells, from about $10^6$ cells to about $5\times10^6$ cells, from about $5\times10^6$ cells to about $10^7$ cells, from about $10^7$ cells to about $5\times10^7$ cells, from about $5\times10^7$ cells to about $10^8$ cells, or from about $5\times10^8$ cells to about $10^9$ cells. Where a subject multi-layer cell unit is roughly spherical, a subject multi-layer cell unit can also be referred to as a "multi-layer cell pellet" or a "multi-layer cell sphere" or a "multi-layer cell spheroid."

The less differentiated cells within a subject multi-layer cell composition are stimulated to differentiate into a more differentiated cell type. For example, depending on the cell type of the more differentiated cell, an MSC can differentiate into a chondrocyte, an osteocyte, a myocyte, a tenocyte, etc.

For example, where a subject multi-layer cell composition comprises NPC and MSC, the MSC within a subject composition are stimulated to differentiate into chondrocytes. For example, after maintaining a subject multi-layer cell composition for a suitable time and under suitable conditions, MSC in the composition differentiate into chondrocytes, e.g., after culturing a subject cell composition for a suitable time and under suitable conditions at least about 2%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, or more than 95% of the MSC differentiate into chondrocytes.

For example, where a subject multi-layer cell composition comprises osteocytes (or osteoblasts) and MSC, the MSC within a subject composition are stimulated to differentiate into osteocytes (or osteoblasts). For example, after maintaining a subject multi-layer cell composition for a suitable time and under suitable conditions, MSC in the composition differentiate into osteocytes (or osteoblasts), e.g., after culturing a subject cell composition for a suitable time and under suitable conditions at least about 2%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, or more than 95% of the MSC differentiate into osteocytes (or osteoblasts).

As another example, where a subject multi-later cell composition comprises myocytes (or myoblasts) and MSC, the MSC within a subject composition are stimulated to differentiate into myocytes (or myoblasts). For example, after maintaining a subject multi-layer cell composition for a suitable time and under suitable conditions, MSC in the composition differentiate into myocytes (or myoblasts), e.g., after culturing a subject cell composition for a suitable time and under suitable conditions at least about 2%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, or more than 95% of the MSC differentiate into myocytes (or myoblasts).

Chondrocytes express one or more of the following markers: 11-fibrau; aggrecan; annexin VI; beta-1 integrin (CD29); cartilage oligomeric matrix protein (COMP); cathepsin B; CD44, CD151, and CD49c; chondrocyte expressed protein-68 (CEP-68); cartilage matrix protein (CMP; matrilin-1); collagen II (type II collagen); collagen IX; Sox9; and collagen X (type X collagen). Chondrocytes can be identified as, e.g., $CD29^+$, $CD90^+$, $CD166^+$, $CD49^+$, $CD44^+$, $CD54^+$, $CD14^-$, $CD34^-$, $CD24^-$, and $CD31^-$. Expression of such markers can be detected using a quantitative polymerase chain reaction (qPCR) assay (e.g., to detect an mRNA marker, or an mRNA encoding a polypeptide marker); an immunoassay using an antibody specific for a polypeptide marker; and the like.

Chondrocytes can be characterized by secretion of one or more of the following: type II collagen; type X collagen; and a proteoglycan such as aggrecan. A subject multi-layer cell composition can induce differentiation of an MSC to a chondrocyte that secretes type II collagen and aggrecan. Aggrecan is a proteoglycan comprising a protein core that is modified with glycosaminoglycans (GAG) such as chondroitin sulfate and keratan sulfate. Whether a chondrocyte secretes aggrecan can be determined by detecting the presence of GAG. GAG can be detected using any known assay, including, e.g., a 1,9-dimethylmethylene blue (DMMB) assay (see, e.g., Oke et al. (2003) *Am. J. Vet. Res.* 64:894); and a safranin-O staining method (see, e.g., Rosenberg (1971) *J. Bone Joint Surg.* 53:69).

Osteocytes express one or more of the following markers: alpha 1(I) procollagen; bone Gla protein (BGP); bone sialoprotein (BSP); Cbfa1/Osf2; collagen type I; E11; osteocalcin; osteopontin; Phex; and RP59. Expression of such markers can be detected using a quantitative polymerase chain reaction (qPCR) assay (e.g., to detect an mRNA marker, or an mRNA encoding a polypeptide marker); an immunoassay using an antibody specific for a polypeptide marker; and the like.

Myocytes include skeletal myocytes. Myocyte-specific markers are known in the art. Skeletal myocyte markers include, e.g., Arpp, Caveolin-3, myosin, nestin, and troponin I.

In some embodiments, e.g., where a subject cell composition comprises chondrocytes, a subject cell composition can produce GAG. For example, a subject cell composition can produce from about 4 μg GAG to about 100 μg GAG per cell composition, e.g., from about 4 μg to about 5 μg, from about 5 μg to about 25 μg, from about 25 μg to about 50 μg, or from about 50 μg to about 100 μg, or more, per cell pellet.

A subject cell composition retains cell viability when cultured in vitro or when introduced into an individual, e.g., when maintained in vivo. For example, at least about 50%, at least about 60%, at least about 75%, at least about 80%, at least about 85%, at least about 90%, or at least about 95%, or more, of the cells in a given cell layer remain viable after at least 2 weeks, at least 4 weeks, or at least 8 weeks in in vitro cell culture or after at least 1 week, at least 2 weeks, at least 4 weeks, or at least 8 weeks, in vivo.

In some instances, a subject cell composition can produce discrete progeny compositions that retain the multi-layer configuration of the original ("parent") cell composition. For example, a subject parent cell composition can include two layers (a bilaminar cell composition), where the composition is roughly spherical, and where a first, inner layer comprises at least about 85% naïve cells (e.g., MSC or other stem cell, as described above), where a second, outer layer comprises at least about 85% "instructive" cells (e.g., NPC, chondroblasts, chondrocytes, osteoblasts, osteocytes, myoblasts, myocytes, or tenocytes), and where the second layer substantially surrounds the first layer. After a period of time in culture in vitro or after a period of time in vivo, the parent cell composition produces a progeny cell composition (referred to in the Examples as a "satellite"), where the progeny cell composition physically separates from the parent cell composition, where the progeny cell composition retains the bilaminar configuration (e.g., discrete first and second layers) of the parent cell composition, and where at least about 50% of the cells in the progeny cell composition remain viable for a period of time of at least two weeks in vitro or in vivo. In some embodiments, a subject cell composition comprises a parent cell composition and one or more progeny cell compositions.

Cells

The less differentiated cells and the more differentiated cells can be obtained from any of a variety of sources. Alternatively, as discussed below, cells can be obtained by inducing a stem cell to differentiate. For example, a stem cell can be induced to differentiate into an NPC, an osteocyte (or an osteoblast), a chondrocyte (or a chondroblasts), a myocyte (or a myoblast), a tenocyte, or an MSC. As noted above, a more differentiated cell includes an NPC, an osteocyte (or an osteoblast), a chondrocyte (or a chondroblasts), a myocyte (or a myoblast), and a tenocyte.

Cells used in a subject cell composition can be obtained from a variety of sources, e.g., from a cadaver, from a living individual, from a post-natal individual, from a juvenile, from an adult individual, from fetal tissue, from a healthy individual, from healthy tissue, from a tissue bank, etc. Cells can be obtained from any form of muscle, from any form of bone, from any form of connective tissue, etc. Cells can be obtained from two or more such sources.

The individual from whom a cell is obtained is generally a mammal, including, e.g., a human, a non-human primate, an ungulate (e.g., a porcine, an ovine, a bovine, etc.), a lagomorph, a rodent (e.g., a murine such as a rat or a mouse), etc. For example, cells (e.g., osteoblasts, osteocytes, chondroblasts, chondrocytes, myoblasts, myocytes, tenocytes, NPC, MSC, etc.) can be isolated from a human, or from a non-human mammal.

Cells can be obtained from any of a variety of sources, as described above. Such cells can be isolated from a source, e.g., isolated such that the desired cell type (e.g., chondrocyte, osteocyte, myocyte, tenocyte, NPC, etc.) is present at from about 75% to about 80%, from about 85% to about 90%, from about 90% to about 95%, or more than 95% purity, e.g., other (non-desired) cell types are present at less than 25%, less than 20%, less than 15%, or less than 5%.

Cells obtained from a source can be expanded in vitro. Cells expanded in vitro will thus include progeny of parent cells isolated from a source, which progeny cells may or may not be genetically identical to the parent cells. However, cells expanded in vitro will substantially retain a phenotype associated with the desired cell type.

Relative to an intended recipient of a subject cell composition, the cells of a subject cell composition can be autologous, allogeneic, or xenogeneic. For example, where the intended or prospective recipient of a subject cell composition is a human, the cells present in the cell composition can be human cells, e.g., isolated from a human or are obtained by inducing human stem cell(s) to differentiate. Where the intended or prospective recipient of a subject cell composition is a human, the cells present in a subject cell composition can be autologous or allogeneic. Where the intended or prospective recipient of a subject cell composition is a human, the cells present in a subject cell composition can in some cases by xenogeneic.

Mesenchymal stem cells (MSC) can be isolated from embryonal mesoderm, placenta, cord blood, from bone marrow (e.g., adult bone marrow), or from fat. Methods of isolating and culturing MSC are known in the art; and any known method can be used to obtain MSC. See, e.g., U.S. Pat. No. 5,736,396, which describes isolation and culture of human MSC; and U.S. Patent Publication No. 2007/0292872. MSC can be identified as Stro-1$^+$, CD106$^+$, CD73$^+$, CD11b$^-$, glycophorin-A$^-$, CD45$^-$, CD34$^-$, CD31$^-$, and CD117$^-$.

NPC can be isolated from the nucleus pulposus of intervertebral discs. Isolation of NPC from intervertebral discs can be carried out using any known method, e.g., a method as described in U.S. Patent Publication No. 2003/0220692. NPC express one or more of the following markers: hypoxia-inducing factor-1 alpha (HIF-1α); hypoxia-inducing factor-1beta (HIF-1β), glucose transporter-1; matrix metalloprotease-2; lactate dehydrogenase-A; and thrombospondin-1.

Osteocytes (or osteoblasts) can be isolated from bone marrow (e.g., human bone marrow), bone marrow stromal cell cultures, human osteoblast explant cultures, or osteocyte (or osteoblast) explant cultures from collagenase-treated bone. See, e.g., Jonsson et al. (1999) *Acta Orthop. Scand.* 70:365. Osteocyte precursor cells can be isolated from bone marrow, e.g., human bone marrow. Osteocytes (or osteoblasts) can be isolated using any known method; see, e.g., U.S. Pat. No. 6,811,776 for methods of isolating and culturing osteocytes.

Chondrocytes can be isolated from bone marrow (e.g., human bone marrow), human bone marrow mesenchymal stromal cells, cartilage (e.g., hyaline cartilage, fibrocartilage, or elastic cartilage), and the like. Additional sources of chondroprogenitor cells include, without limitation, mesenchymal stem cells, cartilage cells, umbilical cord stem cells, bone marrow stromal cells, adipose stromal cells or chondrogenic progenitor cells derived from periosteum or synovium. Chondrocytes can also be isolated and expanded as described in U.S. Pat. No. 7,273,756. Chondrocytes include, but are not limited to, juvenile articular chondrocytes, adult articular chondrocytes, synovial capsule chondrocytes, and periosteum chondrocytes.

Chondroblasts, chondrocytes, osteoblasts, osteocytes, myoblasts, myocytes, and tenocytes can also be generated from MSC using any of various well-known methods, where such methods include, e.g., culturing MSC in the presence of growth factors that promote differentiation of MSC into a more differentiated cell; bioreactor differentiation; and the like. For example, culturing MSC in vitro in a culture medium comprising TGFβ can induce differentiation of chondrocytes; thus chondrocytes can be generated from MSC by culturing the MSC in vitro in a culture medium comprising TGFβ. As another example, osteocytes can be generated from MSC by culturing the MSC in vitro in a culture medium comprising bone morphogenic protein-4 (BMP4). Other methods of inducing osteogenic, tendonogenic, chondrogenic, or myogenic differentiation of an MSC in in vitro culture are known in the art, and any known method can be used; see, e.g., U.S. Patent Publication No. 2007/0292872 and U.S. Pat. No. 5,736,396.

NPC, osteoblasts, osteocytes, chondroblasts, chondrocytes, myoblasts, myocytes, tenocytes, and MSC can be induced from embryonic stem (ES) cells, e.g., an ES cell can be induced to differentiate into an NPC, an osteoblast, an osteocyte, a chondroblast, a chondrocyte, a myoblast, a myocyte, a tenocyte, or an MSC. Methods for inducing differentiation of ES cells in vitro are known in the art. See, e.g., U.S. Patent Publication No. 2006/0057720.

Suitable ES cells include, but are not limited to, any of a variety of available human ES lines, e.g., BG01 (hESBGN-01), BG02 (hESBGN-02), BG03 (hESBGN-03) (BresaGen, Inc.; Athens, Ga.); SA01 (Sahlgrenska 1), SA02 (Sahlgrenska 2) (Cellartis AB; Goeteborg, Sweden); ES01 (HES-1), ES01 (HES-2), ES03 (HES-3), ESO4 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA13 (H13), WA14 (H14) (Wisconsin Alumni Research Foundation; WARF; Madison, Wis.). Cell line designations are given as the National Institutes of Health (NIH) code, followed in parentheses by the provider code. See, e.g., U.S. Pat. No. 6,875,607.

Methods of culturing human ES cells are known in the art. See, e.g., U.S. Pat. No. 6,875,607. Human ES cells can be cultured in vitro using any known method. Suitable human ES cell lines can be positive for one, two, three, four, five, six, or all seven of the following markers: stage-specific embryonic antigen-3 (SSEA-3); SSEA-4; TRA 1-60; TRA 1-81; Oct-4; GCTM-2; and alkaline phosphatase. Human ES cell lines can be negative for SSEA-1.

NPC, osteoblasts, osteocytes, chondroblasts, chondrocytes, myoblasts, myocytes, tenocytes, and MSC can be induced from induced pluripotent stem (iPS) cells e.g., an iPS cell can be induced to differentiate into an NPC, an osteoblast, an osteocyte, a chondroblast, a chondrocyte, a myoblast, a myocyte, a tenocyte, or an MSC. For example, an iPS can be cultured in the presence of one or more osteogenic factors, one or more myogenic factors, one or more tendenogenic factors, or one or more chondrogenic factors.

iPS cells can be generated from mammalian cells (including mammalian somatic cells, such as human somatic cells) using, e.g., known methods. Examples of suitable mammalian cells include, but are not limited to: fibroblasts, skin fibroblasts, dermal fibroblasts, bone marrow-derived mononuclear cells, skeletal muscle cells, adipose cells, peripheral blood mononuclear cells, macrophages, hepatocytes, keratinocytes, oral keratinocytes, hair follicle dermal cells, epithelial cells, gastric epithelial cells, lung epithelial cells, synovial cells, kidney cells, skin epithelial cells, pancreatic beta cells, and osteoblasts.

Mammalian cells used to generate iPS cells can originate from a variety of types of tissue including but not limited to: bone marrow, skin (e.g., dermis, epidermis), muscle, adipose tissue, peripheral blood, foreskin, skeletal muscle, and smooth muscle. The cells used to generate iPS cells can also be derived from neonatal tissue, including, but not limited to: umbilical cord tissues (e.g., the umbilical cord, cord blood, cord blood vessels), the amnion, the placenta, and various other neonatal tissues (e.g., bone marrow fluid, muscle, adipose tissue, peripheral blood, skin, skeletal muscle etc.).

Cells used to generate iPS cells can be derived from tissue of a non-embryonic subject, a neonatal infant, a child, or an adult. In some embodiments, cells used to generate iPS cells are obtained from a post-natal human. Cells used to generate iPS cells can be derived from neonatal or post-natal tissue collected from a subject within the period from birth, including cesarean birth, to death. For example, the tissue source of cells used to generate iPS cells can be from a subject who is greater than about 10 minutes old, greater than about 1 hour old, greater than about 1 day old, greater than about 1 month old, greater than about 2 months old, greater than about 6 months old, greater than about 1 year old, greater than about 2 years old, greater than about 5 years old, greater than about 10 years old, greater than about 15 years old, greater than about 18 years old, greater than about 25 years old, greater than about 35 years old, >45 years old, >55 years old, >65 years old, >80 years old, <80 years old, <70 years old, <60 years old, <50 years old, <40 years old, <30 years old, <20 years old or <10 years old.

In general, cells used to generate iPS cells are substantially genetically identical to a somatic cell from a post-natal human, e.g., are substantially genetically identical to a somatic cell of the post-natal human from which the cell used to generate the iPS cell is derived.

iPS cells produce and express on their cell surface one or more of the following cell surface antigens: SSEA-3, SSEA-4, TRA-1-60, TRA-1-81, TRA-2-49/6E, and Nanog. In some embodiments, iPS cells produce and express on their cell surface SSEA-3, SSEA-4, TRA-1-60, TRA-1-81, TRA-2-49/6E, and Nanog. iPS cells express one or more of the following genes: Oct-3/4, Sox2, Nanog, GDF3, REX1, FGF4, ESG1, DPPA2, DPPA4, and hTERT. In some embodiments, an iPS cell expresses Oct-3/4, Sox2, Nanog, GDF3, REX1, FGF4, ESG1, DPPA2, DPPA4, and hTERT.

Methods of generating iPS cells are known in the art, and a wide range of methods can be used to generate iPS cells. See, e.g., Takahashi and Yamanaka (2006) Cell 126:663-676; Yamanaka et al. (2007) Nature 448:313-7; Wernig et al. (2007) Nature 448:318-24; Maherali (2007) Cell Stem Cell 1:55-70; Maherali and Hochedlinger (2008) Cell Stem Cell 3:595-605; Park et al. (2008) Cell 134:1-10; Dimos et al. (2008) Science 321:1218-1221; Blelloch et al. (2007) Cell Stem Cell 1:245-247; Stadtfeld et al. (2008) Science 322:945-949; Stadtfeld et al. (2008) 2:230-240; Okita et al. (2008) Science 322:949-953.

In some embodiments, iPS cells are generated from somatic cells by forcing expression of Oct-3/4 and Sox2 polypeptides. In some embodiments, iPS cells are generated from somatic cells by forcing expression of Oct-3/4, Sox2 and Klf4 polypeptides. In some embodiments, iPS cells are generated from somatic cells by forcing expression of Oct-3/4, Sox2, Klf4 and c-Myc polypeptides. In some embodiments, iPS cells are generated from somatic cells by forcing expression of Oct-4, Sox2, Nanog, and L1N28 polypeptides.

As an example, iPS cells can be generated from somatic cells (e.g., skin fibroblasts) by genetically modifying the somatic cells with one or more expression constructs encoding Oct-3/4 and Sox2. As one example, somatic cells are genetically modified with one or more expression constructs comprising nucleotide sequences encoding Oct-3/4, Sox2, c-myc, and Klf4. As another example, somatic cells are genetically modified with one or more expression constructs comprising nucleotide sequences encoding Oct-4, Sox2, Nanog, and L1N28.

Cells undergoing induction of pluripotency as described above, to generate iPS cells, can be contacted with additional factors which can be added to the culture system, e.g., included as additives in the culture medium. Examples of such additional factors include, but are not limited to: histone deacetylase (HDAC) inhibitors, see, e.g. Huangfu et al. (2008) Nature Biotechnol. 26:795-797; Huangfu et al. (2008) Nature Biotechnol. 26: 1269-1275; DNA demethylating agents, see, e.g., Mikkelson et al (2008) Nature 454, 49-55; histone methyltransferase inhibitors, see, e.g., Shi et al. (2008) Cell Stem Cell 2:525-528; L-type calcium channel agonists, see, e.g., Shi et al. (2008) 3:568-574; Wnt3a, see, e.g., Marson et al. (2008) Cell 134:521-533; and siRNA, see, e.g., Zhao et al. (2008) Cell Stem Cell 3: 475-479.

Additional Components

A subject multi-layer cell composition can include one or more additional components, where suitable additional components include: a) a buffer; b) an osteogenic factor; c) a chondrogenic factor; d) a myogenic factor; e) a tendonogenic factor; f) a cell culture medium component; g) a scaffold component. Suitable buffers, osteogenic factors, chondrogenic factors, and scaffold components that can be included in a subject multi-layer cell composition are those described below in the context of a cartilage or a bone production composition.

Suitable cell culture medium components are known to those skilled in the art. For example, cell culture medium components as found in any of a variety of standard culture media (e.g., Dulbecco's modified Eagle's medium (DMEM), Roswell Park Memorial Institute 1640 (RPMI 1640), and the like), and can include, e.g., amino acids, glucose, vitamins, salts, sodium pyruvate, and the like. The culture medium can further include albumin.

Method of Making a Multi-Layer Cell Composition

The present disclosure provides methods of making a subject multi-layer cell compositions. The methods generally involve: a) forming a pellet of the first layer cells (e.g., cells of a more differentiated cell type, such as NPC, osteoblasts, osteocytes, chondroblasts, chondrocytes, myoblasts, myocytes, tendocytes, etc.) in a liquid medium in a tube having an inner surface that is substantially non-adherent for the cells; and b) adding the second layer cells (e.g., cells of a less differentiated cell type, such as adult stem cells, embryonic stem cells, iPS cells, MSC, etc.) to the pellet. The pellet becomes suspended in the liquid medium, and the second layer cells adhere to and surround the pellet.

The tube has an inner surface that is substantially non-adherent for the cells, e.g., at least the inner surface of the tube is polypropylene or some other material to which the cells do not readily adhere.

Musculoskeletal Tissue Production Compositions

A subject multi-layer, three-dimensional cell composition is useful for repairing and/or regenerating a musculoskeletal tissue such as an intervertebral disc, bone, skeletal muscle, tendon, or cartilage. For repairing and/or regenerating a musculoskeletal tissue, a subject multi-layer, three-dimensional cell composition can be provided with a biocompatible carrier. For example, one, two, three, four, five, or more (as described elsewhere herein) multi-layer cell composition units are in a composition comprising a biocompatible carrier. A subject musculoskeletal tissue production composition can be used to repair a musculoskeletal tissue, to generate a musculoskeletal tissue, or to fill in missing musculoskeletal tissue. Thus, e.g., a subject cartilage production composition can be used to fill in cartilage, and can also be used to fill in an area in an intervertebral disc.

The present disclosure thus provides compositions comprising: a) a subject multi-layer cells composition; and b) a biocompatible carrier. Depending on the cell types contained within the multi-layer cell compositions, a subject composition will produce cartilage, intervertebral disc tissue, muscle, tendon, or bone. Thus, the present disclosure provides a cartilage production composition comprising: a) a subject multi-layer cells composition, where the first layer includes chondrocytes (and/or chondroblasts) or NPC; and b) a biocompatible carrier. Thus, the present disclosure provides a cartilage production composition comprising: a) a subject multi-layer cells composition, where the first layer includes chondrocytes (and/or chondroblasts) or NPC; and b) a biocompatible carrier. The present disclosure also provides a bone production composition comprising: a) a subject multi-layer cells composition, where the first layer includes osteocytes (and/or osteoblasts); and b) a biocompatible carrier. The present disclosure also provides an intervertebral disc tissue production composition comprising: a) a subject multi-layer cells composition, where the first layer includes NPC; and b) a biocompatible carrier. The present disclosure also provides a muscle production composition comprising: a) a subject multi-layer cells composition, where the first layer includes myoblasts and/or myocytes; and b) a biocompatible carrier. The present disclosure also provides a tendon production composition comprising: a) a subject multi-layer cells composition, where the first layer includes tenocytes; and b) a biocompatible carrier.

A subject cartilage production composition, bone production composition, muscle production composition, tendon production composition, or intervertebral disc tissue production composition can be a liquid at a first temperature, and a solid or a gel at a second temperature. For example, a subject cartilage production composition, bone production composition, muscle production composition, tendon production composition, or intervertebral disc tissue production composition can be a liquid at a first temperature of from about 19° C. to about 30° (e.g., from about 19° C. to about 25° C., or from about 25° C. to about 30° C.); and a solid or a gel at a second temperature of from about 30° C. to about 40° C. (e.g., from about 30° C. to about 35° C., from about 35° C. to about 38° C., or from about 38° C. to about 40° C.).

A subject cartilage production composition, bone production composition, muscle production composition, tendon production composition, or intervertebral disc tissue production composition can be liquid at a first temperature, as noted above, e.g., the composition is injectable through a needle of about 18 gauge, or other conduit (e.g., a tube, a catheter, etc.) having a bore of a similar gauge.

A subject cartilage production composition, bone production composition, muscle production composition, tendon production composition, or intervertebral disc tissue production composition can comprise from about 1 to about 5000 multi-layer cell composition units, e.g., a subject cartilage production composition, bone production composition, muscle production composition, tendon production composition, or intervertebral disc tissue production composition can comprise from about 1 to about 5, from about 5 to about 10, from about 10 to about 50, from about 50 to about 100, from about 100 to about 250, from about 250 to about 500, from about 500 to about 750, from about 750 to about 1000, from about 1000 to about 2000, from about 2000 to about 3000, from about 3000 to about 4000, or from about 4000 to about 5000, multi-layer cell composition units.

A subject cartilage production composition, bone production composition, muscle production composition, tendon production composition, or intervertebral disc tissue production composition will have dimensions, a shape, and a volume that can vary, depending on factors such as the intended treatment site, the intended use, etc. For example, a subject cartilage production composition, bone production composition, muscle production composition, tendon production composition, or intervertebral disc tissue production composition can have a volume of from about 2 $mm^3$ to about 10 $cm^3$, e.g., a subject cartilage production or bone production composition can have a volume in a range of from about 2 $mm^3$ to about 5 $mm^3$, from about 5 $mm^3$ to about 7.5 $mm^3$, from about 7.5 $mm^3$ to about 10 $mm^3$, from about 10 $mm^3$ to about 15 $mm^3$, from about 15 $mm^3$ to about 20 $mm^3$, from about 20 $mm^3$ to about 25 $mm^3$, from about 25 $mm^3$ to about 50 $mm^3$, from about 50 $mm^3$ to about 100 $m^3$, from about 100 $mm^3$ to about 500 $mm^3$, from about 1 $cm^3$, from about 1 $cm^3$ to about 2 $cm^3$, from about 2 $cm^3$ to about 3 $cm^3$, from about 3 $cm^3$ to about 4 $cm^3$, from about 4 $cm^3$ to about 5 $cm^3$ to about 7.5 $cm^3$, or from about $cm^3$ to about 10 $cm^3$.

A subject cartilage production composition, bone production composition, muscle production composition, tendon production composition, or intervertebral disc tissue production composition can have any of a variety of shapes, or can be amorphous. For example, a subject cartilage production composition, bone production composition, muscle production composition, tendon production composition, or intervertebral disc tissue production composition can be in the shape of a disc, or in the shape of a body part to be replaced or repaired. A subject cartilage production composition, bone production composition, muscle production composition, tendon production composition, or intervertebral disc tissue production composition can be amorphous at a first temperature, e.g., before implantation into a treatment site in an individual; and can assume a shape at a second temperature, e.g., at the body temperature of an individual into whom the composition is implanted.

A subject cartilage production composition, bone production composition, muscle production composition, tendon production composition, or intervertebral disc tissue production composition can include one or more scaffold components, as described in more detail below. Where a subject cartilage production composition, bone production composition, muscle production composition, tendon production composition, or intervertebral disc tissue production composition includes one or more scaffold components, the composition can have a certain stiffness, appropriate to the intended use and treatment site. For example, a subject cartilage production composition can have a Young's modulus (or elastic modulus, or modulus of elasticity) in a range of from about 1 megapascal (MPa) to about 50 MPa, e.g., a subject cartilage production composition can have an elastic modulus of from about 1 MPa to about 2 MPa, from about 2 MPa to about 2.5

MPa, from about 2.5 MPa to about 3 MPa, from about 3 MPa to about 4 MPa to about 5 MPa, from about 5 MPa to about 10 MPa, from about 10 MPa to about 20 MPa, from about 20 MPa to about 30 MPa, from about 30 MPa to about 40 MPa, or from about 40 MPa to about 50 MPa. A subject cartilage production composition can have the stated elastic modulus before introduction (e.g., implantation) into a treatment site of an individual and/or after introduction (e.g., implantation) into a treatment site of an individual.

Scaffold Components

A subject cartilage production composition, bone production composition, muscle production composition, tendon production composition, or intervertebral disc tissue production composition can include a scaffold component, e.g., one or more macromolecules that provide support and/or structure and/or chondrogenic or osteogenic conditions to cells within the composition. Macromolecules included in the scaffold can include polypeptides, proteoglycans, polysaccharides, glycosaminoglycans, synthetic polymers, and the like. In certain embodiments, the scaffold is a hydrogel. In certain embodiments, the scaffold is a semi-interpenetrating network hydrogel.

Suitable scaffolds and scaffold components include those described in U.S. Patent Publication Nos. 2006/0293751; 2007/0048291; 2007/0276509; and 2007/098675; and in U.S. Pat. No. 7,241,736.

A scaffold can be in a variety of shapes including sheets, cylinders, tubes, spheres, or beads. A scaffold can also be provided in a shape that provides natural contours of a body part, e.g., a nose or nose part, an ear or ear part, a meniscus, etc.

Suitable scaffolds include, but are not limited to, scaffolds comprising photopolymerizable components; scaffold comprising fibrin glue components (e.g., thrombin and fibrinogen); alginates, including modified alginates; agarose; and collagen scaffolds.

Suitable scaffolds include those that form a hydrogel. The term "hydrogel" as used herein refers to a hydrophilic cross-linked polymer capable of containing a large volume fraction of water. For example, a hydrogel can contain more than about 70%, more than about 75%, more than about 80%, more than about 85%, or more than about 90% water on a volume/volume basis. When a hydrophilic polymer is formed in situ (e.g., in vivo), it can acquire water from its environment or from solutions used to create the hydrogel.

A scaffold can include a glycosaminoglycan (e.g., a polysaccharide comprising a basal structure containing an amino sugar and uronic acid or galactose). Suitable glycosaminoglycans include, but are not limited to, hyaluronic acid, chondroitin, chondroitin sulfate, dermatan sulfate, keratan sulfate, heparin, and heparan sulfate.

Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-polypropylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "cellulose" includes cellulose and cellulose derivatives; similarly, "dextran" includes dextran and dextran derivatives thereof. In certain embodiments, the hydrophilic polymer is a poly(ethylene glycol).

Examples of materials that can be used to form a hydrogel include modified alginates. Alginate is a carbohydrate polymer isolated from seaweed, which can be crosslinked to form a hydrogel by exposure to a divalent cation such as calcium. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemically modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or epsilon-caprolactone. The resulting polymer includes alginate blocks which permit ionically catalyzed gelling, and oligoester blocks which produce more rapid degradation depending on the synthetic design. Alternatively, alginate polymers may be used wherein the ratio of mannuronic acid to guluronic acid does not produce a film gel, which are derivatized with hydrophobic, water-labile chains, e.g., oligomers of epsilon-caprolactone. The hydrophobic interactions induce gelation.

In some embodiments, a scaffold component comprises a moiety comprising an arginine-glycine-aspartic acid (RGD) peptide covalently linked to another component. For example, an alginate can comprise a covalently linked moiety comprising an RGD peptide.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonionic compound, such as mannitol, and then injected to form a gel.

Polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives can also be used. As used herein, the term "hyaluronic acids" refers to natural and chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from commercial sources.

Other polymeric hydrogel precursors include polyethylene oxide-polypropylene glycol block copolymers such as Pluronics™ or Tetronics™, which are crosslinked by hydrogen bonding and/or by a temperature change, as described in Steinleitner et al., Obstetrics & Gynecology, vol. 77, pp. 48-52 (1991); and Steinleitner et al., Fertility and Sterility, vol. 57, pp. 305-308 (1992). Other materials which may be utilized include proteins such as fibrin, collagen, and gelatin. Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as within a few seconds.

Water soluble polymers with charged side groups may be crosslinked by reacting the polymer with an aqueous solution containing ions of the opposite charge, either cations if the polymer has acidic side groups or anions if the polymer has basic side groups. Examples of cations for cross-linking of the polymers with acidic side groups to form a hydrogel are monovalent cations such as sodium, divalent cations such as calcium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

Suitable ionically crosslinkable groups include phenols, amines, imines, amides, carboxylic acids, sulfonic acids and phosphate groups. Negatively charged groups, such as carboxylate, sulfonate and phosphate ions, can be crosslinked with cations such as calcium ions. The crosslinking of alginate with calcium ions is an example of this type of ionic crosslinking. Positively charged groups, such as ammonium ions, can be crosslinked with negatively charged ions such as carboxylate, sulfonate and phosphate ions. In some cases, the negatively charged ions contain more than one carboxylate, sulfonate or phosphate group.

Exemplary anions for cross-linking of the polymers to form a hydrogel are monovalent, divalent or trivalent anions such as low molecular weight dicarboxylic acids, for example, terephthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable membrane. Examples of materials that can be used include polymers having basic reactive groups such as amine or imine groups, e.g., having a molecular weight of between 3,000 daltons and 100,000 daltons, where exemplary polymers include polyethylenimine and polylysine. These are commercially available. An exemplary polycation is poly(L-lysine); examples of synthetic polyamines include polyethyleneimine, poly(vinylamine), and poly(allyl amine). Also suitable for use are naturally-occurring polycations such as chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups. These polymers can be modified to contain active species polymerizable groups and/or ionically crosslinkable groups. Methods for modifying hydrophilic polymers to include these groups are well known to those of skill in the art.

Suitable polymers include natural polymers, semisynthetic polymers, and synthetic polymers. Suitable synthetic polymers include, but are not limited to, polymers or copolymers derived from polydioxane, polyphosphazene, polysulphone resins, poly(acrylic acid), poly(acrylic acid) butyl ester, poly (ethylene glycol), poly(propylene), polyurethane resins, poly (methacrylic acid), poly(methacrylic acid)-methyl ester, poly (methacrylic acid)-n butyl ester, poly(methacrylic acid)-t butyl ester, polytetrafluoroethylene, polyperfluoropropylene, poly N-vinyl carbazole, poly(methyl isopropenyl ketone), poly alphamethyl styrene, polyvinylacetate, poly(oxymethylene), poly(ethylene-co-vinyl acetate), a polyurethane, a poly(vinyl alcohol), and polyethylene terephthalate; ethylene vinyl alcohol copolymer (commonly known by the generic name EVOH or by the trade name EVAL); polybutylmethacrylate; poly(hydroxyvalerate); poly(L-lactic acid) or poly(L-lactide); poly(e-caprolactone); poly(ethylene glycol) (PEG); a derivatized PEG, poly(ethylene glycol) dimethacrylate (PEGDA); poly(lactide-co-glycolide); poly(hydroxybutyrate); poly(hydroxybutyrate-co-valerate); polydioxanone; polyorthoester; polyanhydride; polyethylene terephthalate (PET); polyethylene oxide (PEO), e.g., crosslinkable PEO, non-crosslinkable PEO; poly(glycolic acid) (PGA); poly(D, L-lactide) (PDLL); poly(L-Lactide)(PLL); copolymers of PGA, PDLA, and/or PLA; poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; and carboxymethyl cellulose.

Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers.

Suitable polymers for inclusion in a hydrogel include, but are not limited to, poly(N-isopropylacrylamide); poly(N-isopropylacrylamide-co-acrylic acid); hyaluronic acid or hyaluronate; crosslinked hyaluronic acid or hyaluronate; PHEMA; or copolymers p(NIPAAm)-based sIPNs and other hydrogel sIPNs (semi-interpenetrating networks).

In some embodiments, the hydrogel is a temperature-sensitive hydrogel. In some embodiments, a temperature-sensitive hydrogel is a polyacrylic acid or derivative thereof, e.g., poly (N-isoproylacrylamide) gel, and the increase in temperature causes the hydrogel to contract, thereby forcing the active agent out of the hydrogel. Alternatively, the temperature-sensitive hydrogel is an interpenetrating hydrogel network of poly(acrylamide) and poly(acrylic acid), and the increase in temperature causes the hydrogel to swell. The temperature required for triggering release of an active agent from the hydrogel is generally about normal body temperature, e.g., about 37° C.

Non-limiting examples of suitable scaffold materials are PEGDA and PET, e.g., a scaffold that includes PEGDA and PET; and a sIPN network hydrogel, e.g., a sIPS network hydrogel comprising a non-crosslinkable PEO. For example, a scaffold comprising PEGDA and PET at a ratio of 30:70 provides for good chondrocyte matrix synthesis with sufficient mechanical properties and cell viability.

Collagen

Suitable scaffold components include collagen; a collagen derivative; a methylated collagen; a combination of a collagen or a derivative thereof and a fibrinogen; a combination of a collagen or a derivative thereof and a thrombin; a combination of (a) a collagen or a derivative thereof; (b) a fibrinogen; and (c) a thrombin; a combination of a methylated collagen and a poly(ethylene glycol) or a derivative thereof; atelopeptidic collagen telopeptide collagen crosslinked collagen; and the like.

Fibrin Glue

Suitable scaffold components include fibrin glue components such as fibrinogen and thrombin. For example, a scaffold component can include a fibrinogen component comprising fibrinogen; and a thrombin component comprising thrombin. The fibrinogen component can further include aprotinin, a fibrinolysis inhibitor. The thrombin component can further include $CaCl_2$. The ratio of fibrinogen to thrombin can range from about 0.5:1 to about 2:1, e.g., from about 0.5:1 to about 1:1, from about 1:1 to about 1.5:1, or from about 1.5:1 to about 2:1.

PEG-PEG Polymers

Suitable scaffold components include co-polymers of poly (ethylene glycol) of different molecular weights. For example, a scaffold component can include a first PEG polymer of an average molecular weight in the range of from about 2,000 daltons (Da) to about 10,000 Da; and a second PEG polymer of an average molecular weight in the range of from about 10,000 Da to about 50,000 Da. The first and/or the second PEG polymer can be modified with a glycosaminoglycan, e.g., chondroitin sulfate, heparan sulfate, hyaluronic acid, etc.

An exemplary PEG gel comprises a nucleophilic "8-arm" octomer (PEG-$NH_2$, MW 20 kDa) and a "2-arm" amine-specific electrophilic dimer (SPA-PEG-SPA, MW 3.4 kDa), and is available from Shearwater Corporation, Huntsville, Ala. The addition-elimination polymerization reaction results in a nitrogen-carbon peptide-like linkage, resulting in a stable polymer whose rate of polymerization increases with pH and gel concentration.

Photopolymerizable Polymers

Suitable polymers include synthetic polymers that comprise a photopolymerizable moiety. Suitable polymers include, e.g., water-soluble synthetic polymers including, but not limited to, poly(ethylene oxide) (PEO), poly(ethylene glycol) (PEG), poly(vinyl alcohol) (PVA), poly(vinylpyrrolidone) (PVP), poly(ethyloxazoline) (PEOX) polyaminoacids, pseudopolyamino acids, and polyethyloxazoline, as well as copolymers of these with each other or other water soluble polymers or water insoluble polymers, provided that the conjugate is water soluble. Exemplary photopolymerizable moieties are acrylates, diacrylates, oligoacrylates, methacrylates, dimethacrylates, oligomethoacrylates, or other biologically acceptable photopolymerizable groups.

A synthetic polymer comprising one or more photopolymerizable moieties can be crosslinked via photopolymerization to one or more polysaccharides that are modified with one or more suitable photopolymerization moieties. Suitable polysaccharides include, e.g., alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives, and carrageenan. For example, a polysaccharide can be modified by the addition of carbon-carbon double or triple bond-containing moieties, including acrylate, diacrylate, methacrylate, ethacrylate, 2-phenyl acrylate, 2-chloro acrylate, 2-bromo acrylate, itaconate, oliogoacrylate, dimethacrylate, oligomethacrylate, acrylamide, methacrylamide, styrene groups, and other biologically acceptable photopolymerizable groups.

Initiation of polymerization is accomplished by irradiation with light at a wavelength of between about 200 nm-700 nm, e.g., in the long wavelength ultraviolet range or visible range, e.g., 320 nm or higher, or from about 376 nm to about 514 nm. This light can be provided by any appropriate source able to generate the desired radiation, such as a mercury lamp, long-wave ultraviolet (UV) lamp, He—Ne laser, or an argon ion laser, or through the use of fiber optics.

An example of a water soluble conjugate is a block copolymer of polyethylene glycol and polypropylene oxide, e.g., poly(ethylene glycol) (PEG) polymers that include one or more photopolymerizable moieties that are polymerizable by photoinitiation. For example, a suitable polymer is a PEG polymer that includes one or more polymerizable moieties that are polymerizable by free radical generation, e.g., using visible or long wavelength ultraviolet radiation. One exemplary photopolymerizable PEG polymer is PEG-diacrylate. A suitable PEG polymer has an average molecular weight in a range of from about 2000 daltons (Da) to about 20,000 Da, e.g., from about 2,000 Da to about 4,000 Da, from about 4,000 Da to about 7,000 Da, from about 7,000 Da to about 10,000 Da, from about 10,000 Da to about 20,000 Da, from about 20,000 Da to about 30,000 Da, or from about 30,000 Da to about 40,000 Da. The PEG polymer comprises one or more photopolymerizable moieties, as described above.

A non-limiting example of a suitable polysaccharide is a glycosaminoglycan (e.g., a chondroitin sulfate, a heparan sulfate, a hyaluronic acid, etc.). An example of a chondroitin sulfate is chondroitin-4-sulfate (CS-4) and chondroitin-6-sulfate (CS-6). In some cases, a combination of CS-4 and CS-6 is used. The CS-4/CS-6 mixture can include 10%-90% CS-4 and 10%-90% CS6, e.g., a CS-4/CS-6 mixture can comprise 10%-20% CS-4 and 80%-90% CS-6; 20%-30% CS-4 and 70%-80% CS-6; 30%-40% CS4 and 60%-70% CS-6; 40%-60% CS4 and 40%-60% CS-6; 70%-80% CS-4 and 20%-30% CS-6; or 80%-90% CS4 and 10%-20% CS-6. The chondroitin sulfate is modified with a moiety such as acrylate, diacrylate, methacrylate, ethacrylate, 2-phenyl acrylate, 2-chloro acrylate, 2-bromo acrylate, itaconate, oliogoacrylate, dimethacrylate, oligomethacrylate, acrylamide, methacrylamide, styrene groups, and other biologically acceptable photopolymerizable groups. For example, the CS-4 and the CS-6 can comprise a methacrylate moiety.

Exemplary photopolymerizable polymers includes chondroitin sulfate and a poly(ethylene glycol) as described in, e.g., Varghese et al. (2008) *Matrix Biol.* 27:12-21; Wang et al. (2007) *Nat. Mater.* 6:385; Elisseeff (2008) *Nat. Mater.* 7:271; Hwang et al. (2007) *Methods Mol. Biol.* 407:351.

Buffers

A subject cartilage production composition, bone production composition, muscle production composition, tendon production composition, or intervertebral disc tissue production composition can include, in addition to the above-mentioned cells, a buffer. Suitable buffers include, but are not limited to, (such as N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris (hydroxymethyl)-aminomethane (Tris), etc.).

Chondrogenic Factors

A subject cartilage production composition can include one or more chondrogenic factors, where suitable chondrogenic factors include, but are not limited to, transforming growth factor-beta (TGF-β), e.g., TGF-β1 and/or TGF-β3; inhibin A; chondrogenic stimulating activity factor; bone morphogenic protein-4 (BMP-4); a vitamin A analog, e.g., retinoic acid; a fibroblast growth factor (FGF), e.g., FGF-2; growth and differentiation factor-5 (GDF-5; see, e.g., U.S. Pat. No. 7,198,790); and the like. In some embodiments, a subject cell composition does not include any of the above-listed chondrogenic factors. If present, a chondrogenic factor can be present in a concentration of from about 1 ng/ml to about 100 μg/ml. As an example, TGF-β can be present in a concentration of from about 1 ng/ml to about 10 ng/ml.

Osteogenic-Factors

A subject bone production composition can include one or more osteogenic factors, where suitable osteogenic factors include, but are not limited to, TGF-β1, TGF-β2, TGF-β1.2, vascular endothelial growth factor (VEGF), insulin-like growth factor I or II, bone morphogenic protein (BMP)-2 (BMP2), BMP4, BMP6, and BMP7. If present, an osteogenic factor can be present in a concentration of from about 1 ng/ml to about 100 μg/ml.

Osmolality

In some embodiments, the osmolality of a subject composition is in a range of from about 100 mOsmols/kg to about 1000 mOsmols/kg, e.g., from about 100 mOsmols/kg to about 200 mOsmols/kg, from about 200 mOsmols/kg to about 300 mOsmols/kg, from about 300 mOsmols/kg to about 400 mOsmols/kg, from about 400 mOsmols/kg to about 500 mOsmols/kg, from about 500 mOsmols/kg to about 750 mOsmols/kg, or from about 750 mOsmols/kg to about 1000 mOsmols/kg.

Methods of Producing Cartilage

The present disclosure provides methods of producing cartilage in vitro and/or in vivo, the methods generally involving maintaining a subject cartilage production composition in vitro and/or in vivo under suitable conditions and for a suitable period of time to induce chondrocyte differentiation of an MSC in the cell composition, such that cartilage is produced by the chondrocyte(s). Maintaining a subject cartilage production composition in vitro or in vivo under suitable conditions and for a suitable period of time results in production of cartilage. Cartilage that can be produced and/or repaired using a subject method includes hyaline cartilage, fibrocartilage, and elastic cartilage.

A subject cartilage production composition can be maintained at a temperature of from about 32° C. to about 39° C., e.g., from about 32° C. to about 35° C., from about 35° C. to about 37° C., or from about 37° C. to about 39° C.

A suitable period of time can be a period of time required for at least about 2%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, or more than 95% of the MSC to differentiate into chondrocytes.

A suitable period of time can be a period of time required for production of from about 5 μg GAG (e.g., a GAG associated with aggrecan) to about 10 μg GAG per $0.5 \times 10^6$ cells in the composition.

A suitable period of time can range from about 2 days to about 3 weeks, e.g., from about 2 days to about 5 days, from about 5 days to about 7 days, from about 1 week to about 2 weeks, or from about 2 weeks to about 3 weeks.

A subject cartilage production composition can be maintained in vitro for a first period of time, then maintained in vivo (e.g., maintained in vivo indefinitely). For example, subject cartilage production composition can be maintained in vitro for a first period of time, then introduced into a treatment site in an individual. For example, a subject cartilage production composition can be maintained in vitro for a first period of time of from about 2 days to about 3 weeks, e.g., from about 2 days to about 5 days, from about 5 days to about 7 days, from about 1 week to about 2 weeks, or from about 2 weeks to about 3 weeks; then introduced into a treatment site in an individual.

Alternatively, a subject multi-layer cell composition can be maintained in vitro for a first period of time of from about 2 days to about 3 weeks, e.g., from about 2 days to about 5 days, from about 5 days to about 7 days, from about 1 week to about 2 weeks, or from about 2 weeks to about 3 weeks; and, after the first period of time in vitro, the individual multi-layer cell compositions (e.g., multi-layer cell units) can be used to form a subject cartilage production composition in vitro; then the cartilage production composition can be introduced into a treatment site in an individual.

In some embodiments, a subject multi-layer cell composition is maintained at a pressure that is above atmospheric pressure (e.g., above the average atmospheric pressure at sea level). For example, a subject multi-layer cell composition is maintained in vitro at a pressure of from about 0.5 MPa to about 1 MPa, from about 1 MPa to about 2 MPa, from about 2 MPa to about 3 MPa, from about 3 MPa to about 4 MPa, or from about 4 MPa to about 5 MPa.

As noted above, maintaining a subject cartilage production composition in vitro and/or in vivo for a period of time results in the production of cartilage. Production of cartilage can be measured in various ways, including, e.g., production of proteoglycans (e.g., as measured by GAG); production of collagen (e.g., type II collagen); etc. In some embodiments, a subject method provides for production of from about 5 μg GAG (e.g., GAG associated with aggrecan) to about 10 μg GAG per $0.5 \times 10^6$ cells over a period of time of from about 2 days to about 3 weeks.

A subject cartilage production composition can be introduced into a treatment site, where treatment sites include, e.g., a diarthroidal joint, an intervertebral disc, or any site of cartilage degeneration, cartilage damage, or missing cartilage.

Methods of Producing Intervertebral Disc Tissue

The present disclosure provides methods of producing an intervertebral disc tissue in vitro and/or in vivo, the methods generally involving maintaining a subject intervertebral disc production composition in vitro and/or in vivo under suitable conditions and for a suitable period of time. Maintaining a subject cartilage production composition in vitro or in vivo under suitable conditions and for a suitable period of time results in production of an intervertebral disc tissue. Intervertebral disc tissues include endplate tissue, annulus tissue, and nucleus pulposus tissue. In some embodiments, a subject intervertebral disc composition provides for repair and/or generation of nucleus pulposus tissue.

A subject intervertebral disc production composition can be maintained at a temperature of from about 32° C. to about 39° C., e.g., from about 32° C. to about 35° C., from about 35° C. to about 37° C., or from about 37° C. to about 39° C.

A suitable period of time can be a period of time required for at least about 2%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, or more than 95% of the MSC to differentiate.

A suitable period of time can range from about 2 days to about 3 weeks, e.g., from about 2 days to about 5 days, from about 5 days to about 7 days, from about 1 week to about 2 weeks, or from about 2 weeks to about 3 weeks.

A subject intervertebral disc production composition can be maintained in vitro for a first period of time, then maintained in vivo (e.g., maintained in vivo indefinitely). For example, subject intervertebral disc production composition can be maintained in vitro for a first period of time, then introduced into a treatment site in an individual. For example, a subject intervertebral disc production composition can be maintained in vitro for a first period of time of from about 2 days to about 3 weeks, e.g., from about 2 days to about 5 days, from about 5 days to about 7 days, from about 1 week to about 2 weeks, or from about 2 weeks to about 3 weeks; then introduced into a treatment site in an individual.

Alternatively, a subject multi-layer cell composition can be maintained in vitro for a first period of time of from about 2 days to about 3 weeks, e.g., from about 2 days to about 5 days, from about 5 days to about 7 days, from about 1 week to about 2 weeks, or from about 2 weeks to about 3 weeks; and, after the first period of time in vitro, the individual multi-layer cell compositions (e.g., multi-layer cell units) can be used to form a subject intervertebral disc production composition in vitro; then the intervertebral disc production composition can be introduced into a treatment site in an individual.

In some embodiments, a subject multi-layer cell composition is maintained at a pressure that is above atmospheric pressure (e.g., above the average atmospheric pressure at sea level). For example, a subject multi-layer cell composition is maintained in vitro at a pressure of from about 0.5 MPa to about 1 MPa, from about 1 MPa to about 2 MPa, from about 2 MPa to about 3 MPa, from about 3 MPa to about 4 MPa, or from about 4 MPa to about 5 MPa.

As noted above, maintaining a subject intervertebral disc production composition in vitro and/or in vivo for a period of time results in the production of an intervertebral disc tissue (e.g., nucleus pulposus).

A subject intervertebral disc production composition can be introduced into a treatment site, where treatment sites include, e.g., an intervertebral disc that is damaged or diseased.

Methods of Producing Bone

The present disclosure provides methods of producing bone in vitro and/or in vivo, the methods generally involving maintaining a subject bone production composition in vitro and/or in vivo under suitable conditions and for a suitable period of time to induce osteocyte differentiation of an MSC in the cell composition, such that bone is produced by the osteocyte(s). Maintaining a subject bone production composition in vitro or in vivo under suitable conditions and for a suitable period of time results in production of bone.

A subject bone production composition can be maintained at a temperature of from about 32° C. to about 39° C., e.g., from about 32° C. to about 35° C., from about 35° C. to about 37° C., or from about 37° C. to about 39° C.

A suitable period of time can be a period of time required for at least about 2%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, or more than 95% of the MSC to differentiate into osteocytes.

A suitable period of time can range from about 2 days to about 3 weeks, e.g., from about 2 days to about 5 days, from about 5 days to about 7 days, from about 1 week to about 2 weeks, or from about 2 weeks to about 3 weeks.

A subject bone production composition can be maintained in vitro for a first period of time, then maintained in vivo (e.g., maintained in vivo indefinitely). For example, subject bone production composition can be maintained in vitro for a first period of time, then introduced into a treatment site in an individual. For example, a subject bone production composition can be maintained in vitro for a first period of time of from about 2 days to about 3 weeks, e.g., from about 2 days to about 5 days, from about 5 days to about 7 days, from about 1 week to about 2 weeks, or from about 2 weeks to about 3 weeks; then introduced into a treatment site in an individual.

Alternatively, a subject multi-layer cell composition can be maintained in vitro for a first period of time of from about 2 days to about 3 weeks, e.g., from about 2 days to about 5 days, from about 5 days to about 7 days, from about 1 week to about 2 weeks, or from about 2 weeks to about 3 weeks; and, after the first period of time in vitro, the individual multi-layer cell compositions (e.g., multi-layer cell units) can be used to form a subject bone production composition in vitro; then the bone production composition can be introduced into a treatment site in an individual.

In some embodiments, a subject multi-layer cell composition is maintained at a pressure that is above atmospheric pressure (e.g., above the average atmospheric pressure at sea level). For example, a subject multi-layer cell composition is maintained in vitro at a pressure of from about 0.5 MPa to about 1 MPa, from about 1 MPa to about 2 MPa, from about 2 MPa to about 3 MPa, from about 3 MPa to about 4 MPa, or from about 4 MPa to about 5 MPa.

A subject bone production composition can be introduced into a treatment site, where treatment sites include, e.g., a site of damaged bone; a site of degenerated bone, and a site of diseased bone.

Methods of Producing Muscle

The present disclosure provides methods of producing muscle in vitro and/or in vivo, the methods generally involving maintaining a subject muscle production composition in vitro and/or in vivo under suitable conditions and for a suitable period of time to induce myogenic differentiation of an MSC in the cell composition, such that muscle is produced by the myocytes and/or myoblasts. Maintaining a subject muscle production composition in vitro or in vivo under suitable conditions and for a suitable period of time results in production of muscle.

A subject muscle production composition can be maintained at a temperature of from about 32° C. to about 39° C., e.g., from about 32° C. to about 35° C., from about 35° C. to about 37° C., or from about 37° C. to about 39° C.

A suitable period of time can be a period of time required for at least about 2%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, or more than 95% of the MSC to differentiate into myocytes.

A suitable period of time can range from about 2 days to about 3 weeks, e.g., from about 2 days to about 5 days, from about 5 days to about 7 days, from about 1 week to about 2 weeks, or from about 2 weeks to about 3 weeks.

A subject muscle production composition can be maintained in vitro for a first period of time, then maintained in vivo (e.g., maintained in vivo indefinitely). For example, subject muscle production composition can be maintained in vitro for a first period of time, then introduced into a treatment site in an individual. For example, a subject muscle production composition can be maintained in vitro for a first period of time of from about 2 days to about 3 weeks, e.g., from about 2 days to about 5 days, from about 5 days to about 7 days, from about 1 week to about 2 weeks, or from about 2 weeks to about 3 weeks; then introduced into a treatment site in an individual.

Alternatively, a subject multi-layer cell composition can be maintained in vitro for a first period of time of from about 2 days to about 3 weeks, e.g., from about 2 days to about 5 days, from about 5 days to about 7 days, from about 1 week to about 2 weeks, or from about 2 weeks to about 3 weeks; and, after the first period of time in vitro, the individual multi-layer cell compositions (e.g., multi-layer cell units) can be used to form a subject muscle production composition in vitro; then the muscle production composition can be introduced into a treatment site in an individual.

In some embodiments, a subject multi-layer cell composition is maintained at a pressure that is above atmospheric pressure (e.g., above the average atmospheric pressure at sea level). For example, a subject multi-layer cell composition is maintained in vitro at a pressure of from about 0.5 MPa to about 1 MPa, from about 1 MPa to about 2 MPa, from about 2 MPa to about 3 MPa, from about 3 MPa to about 4 MPa, or from about 4 MPa to about 5 MPa.

A subject muscle production composition can be introduced into a treatment site, where treatment sites include, e.g., a cardiac muscle damage or disease, a site of skeletal muscle damage or disease, a site of smooth muscle damage or disease.

Systems

The present disclosure provides a system for delivering a subject cartilage production composition to a treatment site in an individual. The present disclosure also provides a system for delivering a subject bone production composition to a treatment site in an individual.

A subject system comprises a delivery system that includes an injectable material. The injectable material can comprise: a) a subject multi-layer cell composition; and (b) a scaffold component. Thus, e.g., the injectable material can be a subject bone production composition, a subject cartilage production composition, a subject intervertebral disc tissue production composition, a subject muscle production composition, or a subject tendon production composition. The injectable material can also comprise: a) a first composition comprising a population of less-differentiated cells (e.g., MSC or other stem cell); b) a second composition comprising a population of more-differentiated cells (e.g., NPC, chondroblasts, chondrocytes, osteoblasts, osteocytes, myoblasts, myocytes, or tenocytes), where the first and the second compositions are physically separate from another.

Where a subject system is for delivering a subject cartilage production composition or a subject intervertebral disc tissue production composition to a treatment site in an individual, the system can include an injectable material that comprises: a) a subject multi-layer cell composition, wherein the cells in the first layer are chondrocytes (or chondroblasts) or nucleus pulposus cells; and b) a scaffold component. Where a subject system is for delivering a subject bone production composition to a treatment site in an individual, the system can include an injectable material that comprises: a) a subject multi-layer cell composition, wherein the cells in the first layer are osteocytes (or osteoblasts); and b) a scaffold component. Where a subject system is for delivering a subject muscle production composition to a treatment site in an individual, the system can include an injectable material that comprises: a) a subject multi-layer cell composition, wherein the cells in the first layer are myoblasts or myocytes; and b) a scaffold component. Where a subject system is for delivering a subject tendon production composition to a treatment site in an individual, the system can include an injectable material that comprises: a) a subject multi-layer cell composition, wherein the cells in the first layer are tenocytes; and b) a scaffold component.

A suitable delivery system can include a syringe; a syringe and a needle; a syringe and a catheter; a syringe, a needle, and a catheter; a syringe and a flexible tubing; and the like. A syringe can include a single chamber, or two or more chambers. A suitable delivery system can include two or more syringes, e.g., a suitable delivery system can include two syringes; two syringes and two needles; two syringes, two needles, and a bifurcated tube; and the like.

A scaffold component can include two or more components that, when combined, result in formation of a macromolecular structure. An example is fibrin glue. For example, a scaffold component can comprise a first precursor material and a second precursor material; and the delivery system can include i) a first chamber comprising a subject multi-layer cell composition and the first precursor material; and ii) a second chamber comprising the second precursor material. In this example, the delivery system is adapted to mix the contents of the first chamber and the second chamber prior to delivery to the treatment site. As an example, the first precursor material comprises fibrinogen, and the second precursor material comprises thrombin. Alternatively, the first precursor material could be the thrombin component; and the second precursor material could be the fibrinogen component. Dual-chamber delivery systems are known in the art; for example, dual-chamber delivery systems that are suitable for use are described in, e.g., U.S. Pat. No. 6,454,786; U.S. Pat. No. 6,461,325; and U.S. Pat. No. 5,585,007.

Another example of a dual-chamber delivery system is one that comprises: a) a first composition comprising a population of less-differentiated cells (e.g., MSC or other stem cell); b) a second composition comprising a population of more-differentiated cells (e.g., NPC, chondroblasts, chondrocytes, osteoblasts, osteocytes, myoblasts, myocytes, or tenocytes), where the first and the second compositions are physically separate from another, e.g., each in separate chambers of the dual-chamber delivery system. The ratio of the less-differentiated cells to the more-differentiated cells is generally greater than 1:1, as described above. The first composition and the second composition are maintained in separate chambers, then mixed just prior to introduction into a treatment site. A scaffold component can then be applied to the cells after introduction into the treatment site.

A scaffold component can include a first scaffold component that is a synthetic polymer comprising a photopolymerizable moiety and a second scaffold component comprising a photopolymerizable moiety. Suitable photopolymerizable components are described supra.

Suitable delivery systems include, e.g., a syringe or other vessel; and a needle or other conduit for introducing a subject bone production or cartilage production composition into a treatment site. A syringe can include a single chamber. A syringe can include two or more chambers. Alternatively, a suitable delivery system can include two syringes, each holding a composition to be admixed.

Utility

A subject multi-layer cell composition is useful for producing a subject cartilage production composition, a subject bone production composition, a subject intervertebral disc tissue production composition, a subject muscle production composition, or a subject tendon production composition. A subject cartilage production composition is useful for replacing, repairing, or regenerating cartilage in vivo, e.g., in an individual in need of cartilage replacement, repair, or regeneration. A subject intervertebral disc tissue production composition is useful for replacing, repairing, or regenerating intervertebral disc tissue in vivo, e.g., in an individual in need of replacement, repairing, or regeneration of intervertebral disc tissue. A subject bone production composition is useful for replacing, repairing, or regenerating bone in vivo, e.g., in an individual in need of bone replacement, repair, or regeneration. A subject cartilage production composition or a subject bone production composition can be introduced into a treatment site in an individual using a subject system for delivering such a composition. A subject muscle production composition is useful for replacing, repairing, or regenerating bone in vivo, e.g., in an individual in need of muscle replacement, repair, or regeneration. A subject tendon production composition is useful for replacing, repairing, or regenerating bone in vivo, e.g., in an individual in need of tendon replacement, repair, or regeneration.

Cartilage Regeneration, Replacement, and Repair

As discussed above, a subject cartilage production composition is useful for replacing or regenerating cartilage in vivo, e.g., in an individual in need of cartilage replacement and/or regeneration. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a taxation of a joint by a torn ligament, malignment of joints, bone fracture, or by hereditary disease. A subject cartilage regenerative method is also useful for remodeling cartilage matrix, such as in plastic or reconstructive surgery, as well as in periodontal surgery. A subject cartilage regenerative method can be used in conjunction with a reparative procedure, e.g., surgical repair of a meniscus, ligament, or cartilage.

As discussed above, in some instances, a subject cartilage production composition will include one or more scaffold components that are photopolymerizable. In such instances, a subject treatment method can involve: a) introducing a subject cartilage production composition into a treatment site in an individual; and b) exposing the introduced composition to a wavelength of light for such a time as to effect polymerization of the scaffold components.

As discussed above, in some instances a subject cartilage production composition will include two components that, when mixed, will form a fibrin glue. In such instances, a subject treatment method can involve: a) admixing a first composition comprising thrombin with a second composition comprising fibrinogen, where one of the compositions also includes a subject multi-layer cell composition, where the mixing results in a cartilage production admixture composition; and b) introducing the admixture composition into a treatment site in an individual. The time that elapses between the admixing and the introducing steps can be less than about 5 minutes.

A subject cartilage production composition can be introduced into an individual in need thereof to regenerate cartilage of a diarthroidal joint, such as a knee, an ankle, an elbow, a hip, a wrist, a knuckle of a finger, a knuckle of a toe, or a temporomandibular joint. The treatment can be directed to the meniscus of the joint, to the articular cartilage of the joint, or both. As another example, a subject cell composition can be used to treat a degenerative disorder of a knee, e.g., where the degenerative disorder is the result of traumatic injury (e.g., a sports injury or excessive wear) or osteoarthritis.

As another example, a subject cartilage production composition is introduced into an intervertebral disc, to treat degeneration of an intervertebral disc, and disorders resulting from degeneration of an intervertebral disc.

A subject cartilage production composition is useful to enhance attachment of a prosthetic device implanted in an individual. A subject cartilage production composition can also form a part of a prosthetic device, to be implanted into an individual. Prosthetic devices include, but are not limited to, an artificial meniscus, an artificial tendon, an artificial ligament, etc.

A subject cartilage production composition can be used for remodeling cartilage matrix, such as in plastic or reconstructive surgery. For example, a subject cartilage production composition can be used for remodeling cartilage in the external ear, in the nose, and the like.

Bone Regeneration, Replacement, and Repair

As discussed above, a subject composition (e.g., a subject bone production system) is useful for repairing damaged bone or disease bone, and for replacing missing bone. For example, a subject bone production composition is useful for treating osteoporosis, for repairing bone fractures, and for carrying out bone reconstruction.

Muscle Regeneration, Replacement, and Repair

As discussed above, a subject composition (e.g., a subject muscle production system) is useful for repairing damaged or disease muscle. Diseased muscle tissue includes ischemic cardiac muscle tissue; torn or otherwise damaged skeletal muscle tissue; diseased muscle tissue; etc.

Subjects

Individuals who are suitable recipients for a subject cartilage production composition include, but are not limited to, individuals suffering from intervertebral disc degeneration; individuals suffering from arthritis of a joint, e.g., a diarthroidal joint; individuals in need of hip replacement; individuals in need of a prosthetic device; and individuals in need of tissue reconstruction, e.g., cartilage reconstruction.

Individuals who are suitable recipients for a subject bone production composition include, but are not limited to, individuals who have suffered a bone fracture but who are otherwise healthy; individuals who have suffered a bone fracture and who have osteogenesis imperfecta; individuals who have suffered bone loss due to osteoporosis; and individuals who have suffered bone loss due to trauma, or due to a surgical treatment.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second (s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Culturing MSCs in a Bioreactor

Chondrogenic stimulation: bone marrow-derived MSCs (Cambrex Corp.) were suspended in 1.2% alginate gel at a concentration of 4 million cells/mL; beads were formed by dispensing dropwise into a calcium chloride bath. Beads were cultured in media with chondrogenic supplements and TGF-beta3 for 7 or 14 days.

Bioreactor assembly: a dialysis cassette (Slide-A-Lyzer, Pierce) was filled with 300 uL of hyaluronan gel and submerged in cell culture media to allow for volume expansion and pressure buildup. An autoclavable porous metal clip surrounds the device to permit fluid exchange but prevent membrane rupture).

Undifferentiated MSCs or MSCs pre-cultured in alginate beads were suspended in fibrin glue (Tisseel VH, Baxter Corp.) at a concentration of $4 \times 10^6$ cells/mL and a 100 μL pellet was injected into the center of the cassette. Cassettes were cultured in media without chondrogenic supplements for 1 or 2 weeks. In addition to cell viability and histology, total proteoglycan content was assessed by dimethylmethylene blue (DMMB).

Cell viability of bioreactor cell pellets was improved when cells were pre-treated; groups E-H (Table 1) had 90-97% viability while groups A-D had 80-85% viability.

TABLE 1

| Group | Pretreatment | Time in bioreactor | Average total GAG content (μg) |
|---|---|---|---|
| A | none | 1 week | 38 ± 16 (n = 2) |
| B | none | 2 weeks | 108 ± 66 (n = 6) |
| C | none | 3 weeks | 150 ± (n = 5) |
| D | none | 4 weeks | 255 (n = 1) |
| E | 1 week | 1 week | 109 ± 62 (n = 5) |
| F | 1 week | 2 weeks | 190 ± (n = 6) |
| G | 2 weeks | 2 weeks | 251 ± (n = 5) |
| H | 3 weeks | 2 weeks | 220 ± (n = 2) |

Total glycosaminoglycan (GAG) content increased with increasing bioreactor culture time (Table 1); the change is significant when bioreactor culture time is doubled for cells that have been differentiated for 1 week prior to culture (group E vs. F, p<0.03). Although there was a trend of increasing GAG content with increased differentiation time (groups F vs. G vs. H) the change was not significant.

Safranin-O staining of fibrin-cell pellets showed little or no staining for undifferentiated groups cultured up to three weeks. After four weeks of culture, pellets showed isolated areas of faint staining. Groups pre-treated for one week before bioreactor culture also showed no staining, but robust staining was seen in group G.

Example 2

Co-Culturing NPC and MSC

NPC and adult MSC were co-cultured in a 3-dimensional bi-layer culture system. The 3-dimensional system is a spherical, bilayer pellet with an inner sphere and an outer shell. Human MSC were obtained from a commercial source; NPC were obtained from mature bovine tail discs. One cell type was labeled with DiO. The bilayer pellet was formed in two centrifugation steps. Cells forming the inner sphere were centrifuged in 2 ml culture medium at 400×g for 5 minutes in a 15-ml polypropylene tube. Cells forming the outer layer of the pellet were pipetted into the tube; and the cells were centrifuged at 400×g for 5 minutes. Within 24 hours, the cells formed a rounded pellet that freely floated in the tube. Each pellet included about $5 \times 10^5$ cells.

Each pellet was cultured for 7 days, 14 days, or 21 days. After 7 days, 14 days, or 21 days, the cells in the pellets were sorted by fluorescence activated cell sorting into MSC and NPC. The sorted cells were assayed for levels of collagen type 2, aggrecan, and SOX9 using quantitative polymerase chain reaction. The amount of aggrecan produced (as assessed by GAG detection) was measured using a DMMB assay. The experimental groups are depicted schematically in FIG. 1.

After 14 days, a spherical bi-layer pellet with MSC on the inside and NPC on the outside at a ratio of 25/75 produced significantly more GAG than all other conformations and ratios as measured by DMMB. MSC experienced signaling originating from the center of the pellet spreading outwards as well as signaling from the interface of the two cell types propagating inwards.

Example 3

Structured Coculture of Adult Stem Cells and Nucleus Cells for Disc Regeneration Materials and Methods
Cell Culture Bovine NPC were isolated from caudal discs of healthy adult cows within 48 hours of sacrifice. The NP tissue was carefully separated by gross dissection and digested in 0.5% collagenase/dispase and 2% antibiotic/antimycotic in low glucose Dulbecco's Modified Eagle Medium (DMEM) at 37° C. for 4-6 hrs with constant stirring. The cells were then plated in tissue culture flasks and expanded to the fourth passage in NPC Media (DMEM with 1% antibiotic/antimycotic, 1.5% 400 m Osmolarity, and 5% Fetal Bovine Serum (FBS)) at 37° C. with 5% $CO_2$. Culture media was changed twice a week.

Commercially available human MSC were purchased (Lonza) and expanded to the sixth passage in monolayer culture using growth media (DMEM low glucose with 1% antibiotic/antimycotic and 10% FBS) at 37° C. with 5% $CO_2$. Culture media was changed twice a week.

Human nucleus pulposus samples were obtained from a consenting 55 year-old female patient undergoing surgery for scoliosis. The tissue was digested and the cells expanded. In addition, bovine MSC were isolated from femur tissue and the cells were expanded.

Bilaminar Pellet Formation

Human MSC and bovine NPC were used to make coculture pellets. The cross-species human-MSC/bovine-NPC pellets enabled one to trace the location of the cells via their lineage. Three different types of pellets were formed, each consisting of 500,000 cells total: pellets of 100% one cell type, pellets of MSC and NPC with randomized organization, and pellets of MSC and NPC organized into a bilaminar. The pellets containing both MSC and NPC were formed with three different cell number ratios of 25/75, 50/50, and 75/25 respectively (FIG. 1). To produce the 100% one cell type pellets, 500,000 cells were pipetted into a 15 mL polypropylene tube and centrifuged at low speeds (300 g) for 5 min. To create the randomized pellets, both cell types were added to the same tube, pipetted to ensure thorough mixing, and centrifuged at low speed for 5 min. In order to form the bilaminar organized pellets, the cell type that would form the inner sphere of the pellet was added to a 15 mL polypropylene tube and centrifuged at low speed for five minutes. Subsequently, the second cell type that would form the outer shell was gently added to the same tube. The cells were then centrifuged again at low speed for 5 min. Organized pellets were formed for all three ratios with MSC on the inside and NPC on the outside and vice versa. All pellets were cultured in 2 mL of growth media for three days with caps loosened to allow for gas exchange. After three days, the pellets became spherical and were transferred to ultra-low attachment 24 well plates (Corning) for the remainder of their culture time. Media were changed three times a week.

Same-species pellets were also made, as controls for species interactions. Pellets with human MSC and human NPC were made; and pellets with bovine MSC and bovine NPC were made.

Histology
Cell Lineage Tracing for Frozen Sections

Before being pelleted, cells were labeled with fluorescent cell membrane markers (either DiO or DiI, Invitrogen). After the pellets had reached their desired culture time, they were embedded in OCT Tissue-Tek (Sakura Finetek) and frozen sectioned at 7 nm using a cryostat. Sections were then counterstained with the Hoescht dye, a fluorescent nuclear marker (Sigma). Images were taken using epi-fluorescent microscopy.

Immunohistochemistry with Paraffin Sections

At the end of the culture time, the pellets were fixed in 10% Buffered Formalin overnight and processed for paraffin sectioning at 7 nm thickness. At this stage, the sections were immuno-stained using the human specific antibodies Lamp1 and Lamp2 (Abcam). The sections were then counterstained with hematoxylin.

Results
NPC Culture

The NPC started as small rounded cells. They often required several days to attach to the tissue culture flask. Many of the cells never attached at all and were discarded. Though the cells were initially seeded in very small flasks (12.5 $cm^2$, Falcon), it took up to 2 weeks for the cells to reach confluence. Once the cells were confluent and passaged, their growth rate significantly increased, and they were easily expanded to the fourth passage.

Macroscopic Observations

Immediately after centrifugation the pellets appeared flattened. Spheres formed within 48 hours and reached a maximum size of approximately 2 mm in diameter. After one week of culture, coculture pellets began to exhibit budding (FIGS. 2A-D). During the course of the second week of culture, these buds separated from the main pellet entirely to form numerous independent satellite pellets of various sizes. As the satellite pellets budded off of the main pellet, the main pellet did not noticeably decrease in size. At the three week time point, several of the larger satellite pellets also began to exhibit budding.

The 100% MSC pellets did not exhibit budding nor did any satellite pellets form at any point. The 100% NPC pellets exhibited budding and satellite pellet formation on the same time frame as the coculture pellets (in this case the satellite pellets were composed entirely of NPC). The same-species pellets (e.g. human-MSC and human-NPC) exhibited the same behavior as the cross-species pellets (human-MSC and bovine-NPC). There was no difference in the budding or satellite formation rate between the bilaminar coculture pellet and the random coculture pellets.

Histology

Figure 5A:
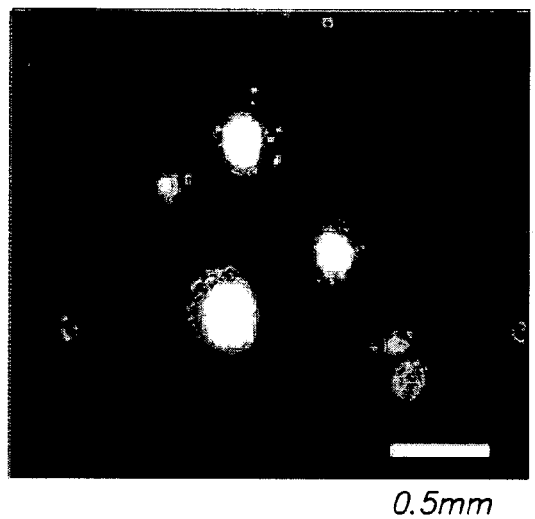
FIGS. 5A and 5B depict fluorescent microscopy image (FIG. 5A) and immunohistochemistry staining (FIG. 5B) of a satellite pellet.
Figure 5B:
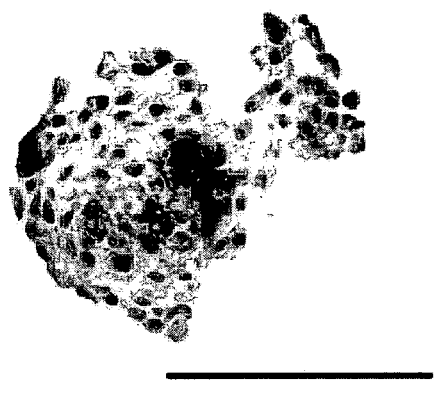

Both the frozen (FIGS. 3A and 3B) and paraffin histological sections confirmed that the main pellets maintained their structure throughout the culture time even as satellite pellets budded off them (FIG. 4). The histology of the satellite-pellets confirmed that they were composed of both cell types. Most surprisingly, the satellite pellets appear to all have the same structure with MSC on the inside and NPC on the outside (FIG. 5A, 5B). This structural organization was independent of the structure and ratio of the main pellet that from which the pellets stemmed.

FIGS. 2A-D. (A) Coculture pellet after three days of culture. (B) A budding coclature pellet at one week of culture. (C) Coculture pellet after three weeks, several satellite pellets have formed and separated. (D) A budding satellite pellet after three weeks of culture.

FIGS. 3A and 3B. Frozen sections of bilaminar pellets after 3 weeks of culture. All cell nuclei are labeled with Hoescht dye (blue in original). A) Bilaminar pellet with MSC unstained and NPC dyed with DiI (red). The pellet is organized with 50% MCS on the inside and 50% NPC on the outside. B) Bilaminar pellet with MSC dyed with DiO (green in original) and NPC unstained. The pellet is organized with 75% MSC on the inside and 25% NPC on the outside.

FIG. 4. Three week bilaminar pellet with MSC on the inside (brown in original) and NPC on the outside after undergoing budding and satellite pellet formation. This is a paraffin section stained using immunohistochemistry with the human specific antibodies (darker; brown in original), Lamp1 and Lamp2, and counterstained with hematoxylin (lighter; blue in original). It is apparent that at three weeks, after undergoing budding numerous times, the pellet conserved it's original structure of having MSC on the inside and NPC on the outside.

FIGS. 5A and 5B. (A) Fluorescent microscopy image of a satellite pellet frozen section. MSC were pre-stained with DiO (green in original) before forming the main pellet. These satellite pellets formed from a random 50/50 coculture pellet. Here the center of the satellite pellet is clearly stained with DiO while the exterior is free of dye indicating that it is composed of both cell types and has the bilaminar organization of MSC inside and NPC outside. (B) Immunohistochemistry performed on a paraffin section of a satellite pellet also formed from a random 50/50 coculture pellet. The MSC at the center of the satellite pellet are stained with a human specific antibody (brown in original) and counterstained with hematoxylin. Once again, this demonstrates the bilaminar structure of the satellite pellets which have MSC on the inside and NPC on the outside.

Example 4

Further Characterization of Cell Pellets

Bi-layer cell pellets were made as described above, with MSC ("naïve" cells) and NPC ("instructive" cells). Various parameters—including number of cells per pellet, GAG content per pellet—were measured as a function of 1) the ratio of MSC to NPC; 2) the configuration of MSC and NPC; 3) time in culture; 4) and presence of FBS in the culture medium. The results are shown in FIGS. 6-9.

Figure 6:
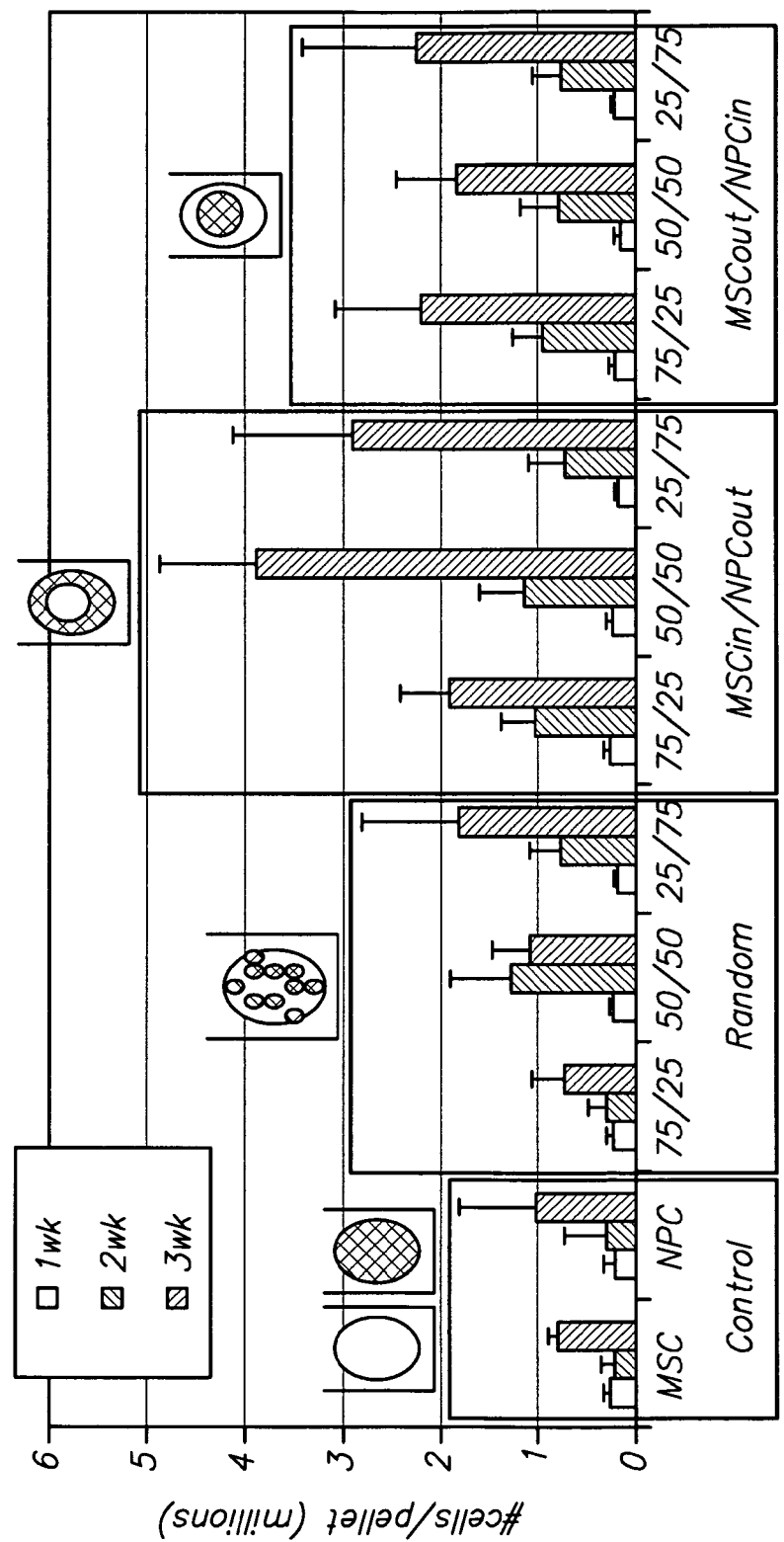
FIG. 6 is a graph depicting the number of cells per pellet after time in in vitro culture for cell compositions of various ratios of MSC to NPC, and various configurations.

FIG. 6 provides a graph of the DNA content at 1 week (wk), 2 wk, 3 wk of culture measure with Pico-green assay. The DNA content can be converted into the number of cells that were present in each pellet at the end of the culture time. All of the pellets started off with 0.5 million cells. Thus, this is a measure of the amount of cell proliferation at the different time points for the different groups. As shown in FIG. 6, the groups with the most cell proliferation (highest DNA content at 3 weeks) are those with MSC on the inside and NPC on the outside.

Figure 7:
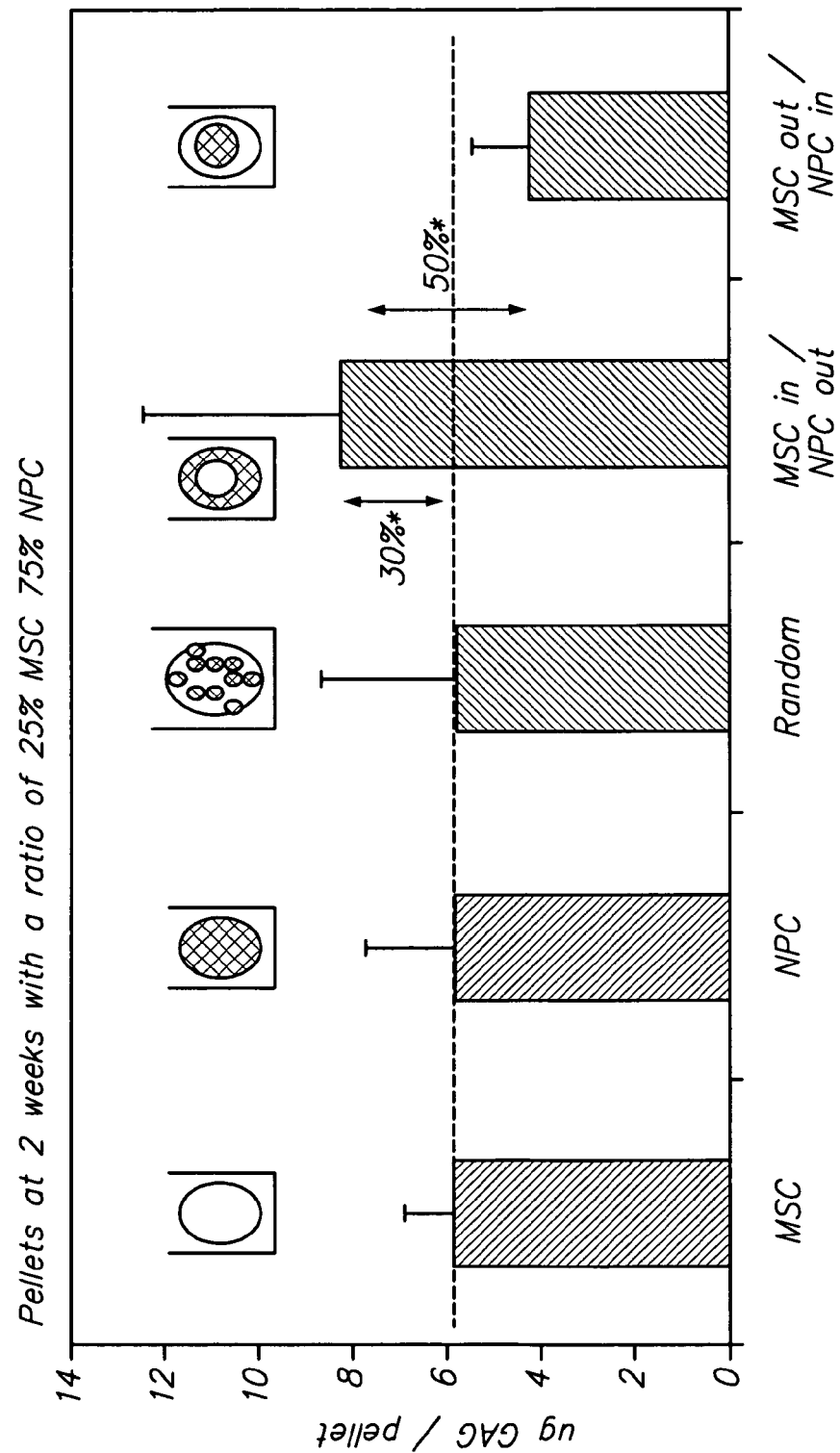
FIG. 7 is a graph depicting the amount of glycosaminoglycan (GAG) produced per cell pellet at 2 weeks in in vitro culture.

FIG. 7 provides a graph of the GAG content as measured by dimethylmethylene blue (DMMB) assay. GAG refers to proteoglycan, one of the most important proteins in cartilage and intervertebral disc; the data are reported as GAG per pellet. FIG. 7 provides the results for the ratio of MSC 25% and NPC at 75% after 2 wk of culture. FIG. 7 shows that the bilayer pellet with MSC on the inside made at least 30% more GAG than all other pellets. Asterisks denote statistically significant data.

Figure 8A:
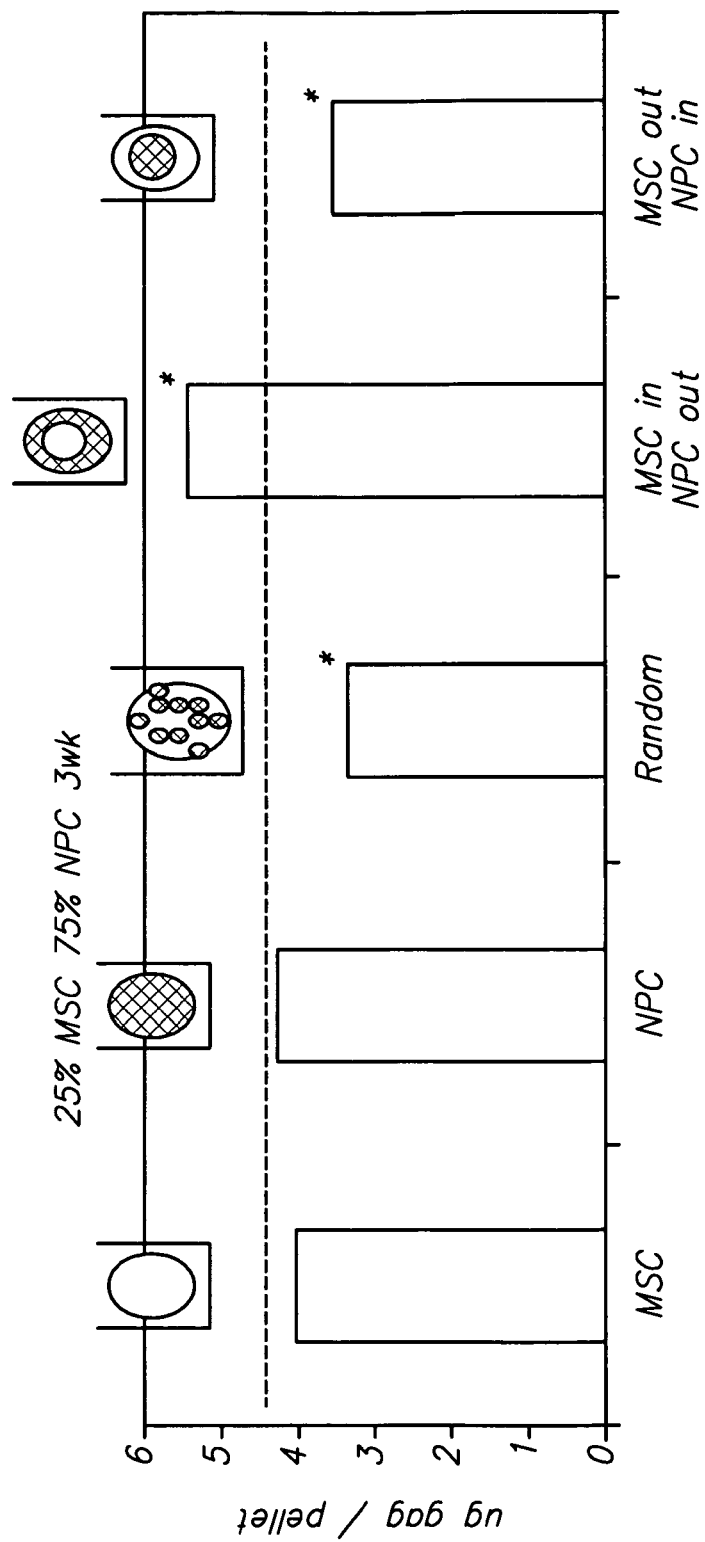
FIGS. 8A and 8B are graphs depicting the amount of GAG produced per cell pellet at 3 weeks in in vitro culture.
Figure 8B:
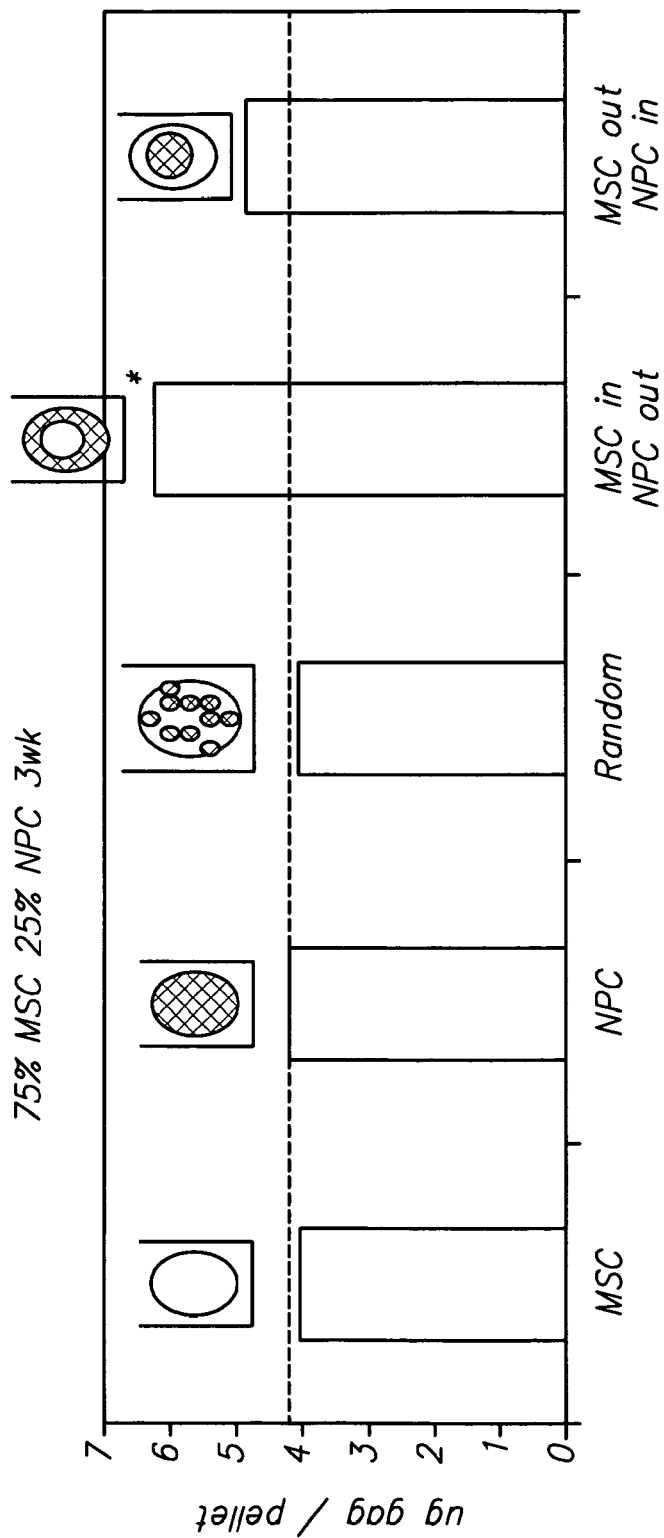

FIGS. 8A and 8B. FIG. 8A provides a graph similar to that shown in FIG. 7 except that the data in FIG. 8A are for 3 wk time point. FIG. 8A shows that the bilayer pellet with MSC inside produced the most GAG per pellet. Asterisks denote statistically significant data. FIG. 8B provides a graph showing data for the 3 wk time point with the ratio of 75% MSC and 25% NPC.

Figure 9:
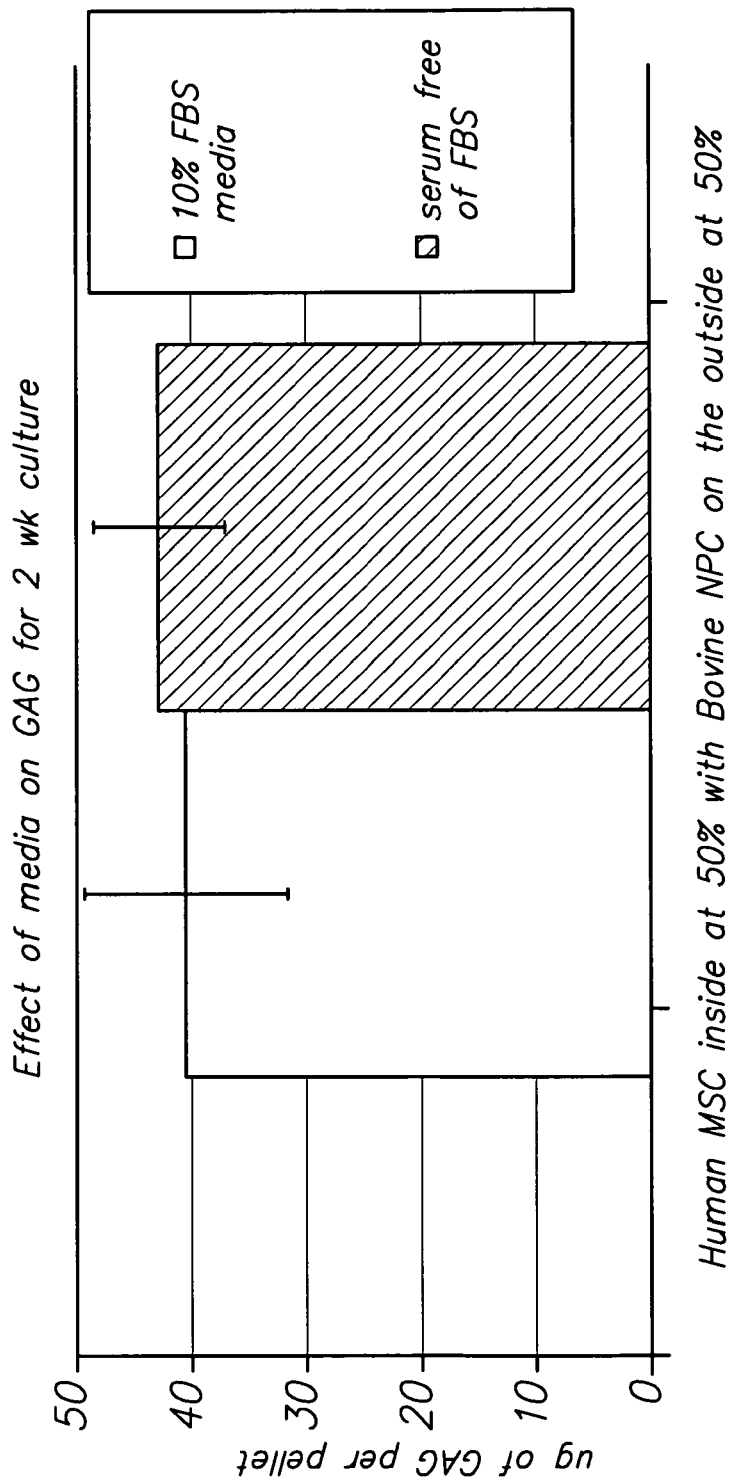
FIG. 9 depicts the amount of GAG produced per cell pellet in serum-free culture medium, or in culture medium containing 10% fetal bovine serum.

FIG. 9 depicts GAG production after two weeks of culture in media that contains 10% FBS and media that does not contain FBS. The data presented in FIG. 9 demonstrates that the culture medium does not have any significant effect on GAG production by the bilaminar cell pellets.

Example 5

In Vivo Studies

An intervertebral disc of a rat was denucleated. A bilaminar cell pellet containing human MSC and bovine NPC at a 50:50 ratio was inserted into the site of denucleation, fibrin was added, and the annulus sutured. Two weeks later, the rat was sacrificed, and histological analysis of the disc was carried out. FIG. 10A presents a view of the whole disc, showing the endplate, the annulus, and nucleus pulposus space. FIG. 10B is a view of the nucleus pulposus space from FIG. 10A. The pellet is seen on the right, and native tissue on the left. At the two-week time point, the pellet remained intact, the cells appeared to be viable, and the pellet and native tissues were merging.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A multi-layer three-dimensional cell composition comprising:
   a) a first layer comprising a plurality of cells, wherein at least about 85% of the cells in the first layer are nucleus pulposus cells (NPC), chondroblasts, chondrocytes, osteoblasts, osteocytes, myoblasts, myocytes, or tenocytes; and
   b) a second layer comprising a plurality of cells, wherein at least about 85% of the cells in the second layer are mesenchymal stem cells (MSC),
   wherein the composition has a substantially spherical form, and wherein the second layer is completely surrounded by the first layer.

2. The cell composition of claim 1, wherein the cells of the first layer are obtained from donor tissue or are differentiated from a stem cell in vitro.

3. The cell composition of claim 1, wherein the composition has a unit volume of from about 0.05 mm$^3$ to about 0.5 cm$^3$.

4. The cell composition of claim 1, wherein the ratio of cells in the first layer to MSC in the composition is 1:1.

5. The cell composition of claim 1, wherein the ratio of cells in the first layer to MSC in the composition is greater than 1:1.

6. The cell composition of claim 1, wherein the ratio of MSC to cells in the first layer in the composition is 1:1.

7. The cell composition of claim 1, wherein the cells are present in the composition at a density of about $0.05 \times 10^6$ cells per mm$^3$ to about $10^7$ cells per mm$^3$.

8. The cell composition of claim 1, wherein the MSC are isolated from a naturally-occurring source, or are derived by inducing a stem cell to differentiate into an MSC in vitro.

9. A musculoskeletal tissue production composition comprising:
   a) a multi-layer cell composition of claim 1; and
   b) a biologically compatible carrier.

10. The composition of claim 9, wherein the biologically compatible carrier comprises a scaffold component.

11. A cartilage production composition comprising:
    a) a multi-layer cell composition of claim 1, wherein the cells in the first layer are chondrocytes and/or chondroblasts; and
    b) a biologically compatible carrier.

12. The composition of claim 11, wherein the biologically compatible carrier comprises a scaffold component.

13. The composition of claim 11, wherein the composition comprises from about 1 multi-layer cell compositions to about 10$^3$ multi-layer cell compositions.

14. The composition of claim 11, wherein the composition is liquid at 22° C., and wherein said liquid forms a solid or semi-solid at 37° C.

15. The composition of claim 12, wherein said scaffold component is one or more of poly(ethylene glycol), a glycosaminoglycan, a fibrin glue component, an alginate, an agarose, and a collagen.

16. The composition of claim 12, wherein said scaffold component comprises a chondroitin sulfate component and/or a poly(ethylene glycol) component.

17. The composition of claim 16, wherein the chondroitin sulfate component comprises chondroitin-4-sulfate and chondroitin-6-sulfate.

18. The composition of claim 16, wherein the poly(ethylene glycol) component has an average molecular weight in the range of from about 2000 to about 10,000.

19. The composition of claim 11, further comprising at least one chondrogenic factor.

20. The composition of claim 19, wherein the at least one chondrogenic factor is one or more of a transforming growth factor-beta, inhibin A, chondrogenic stimulating activity factor, bone morphogenic protein-4, a vitamin A analog, growth and differentiation factor-5, and a fibroblast growth factor.

21. An intervertebral disc tissue production composition comprising:
a) a multi-layer cell composition of claim 1, wherein the cells in the first layer are NPC; and
b) a biologically compatible carrier.

22. The composition of claim 21, wherein the biologically compatible carrier comprises a scaffold component.

23. A muscle production composition comprising:
a) the multi-layer cell composition of claim 1, wherein the cells in the first layer are myoblasts or myoctes; and
b) a biologically compatible carrier.

24. The composition of claim 23, wherein the biologically compatible carrier comprises a scaffold component.

25. A bone production composition comprising:
a) a multi-layer cell composition of claim 1, wherein the cells in the first layer are osteoblasts; and
b) a biologically compatible carrier.

26. A system for delivering a musculoskeletal tissue-producing composition to a treatment site in an individual, the system comprising a delivery system comprising an injectable material, wherein the injectable material comprises:
a) a multi-layer cell composition of claim 1; and
b) a scaffold component.

27. The system of claim 26, wherein the scaffold component comprises a first precursor material and a second precursor material, and wherein the delivery system comprises:
i) a first chamber comprising the multi-layer cell composition and the first precursor material; and
ii) a second chamber comprising the second precursor material,
wherein the delivery system is adapted to mix the contents of the first chamber and the second chamber prior to delivery to the treatment site.

28. The system of claim 26, wherein the first precursor material is fibrinogen and wherein the second precursor material is thrombin.

29. The system of claim 26, wherein the scaffold component comprises a synthetic polymer comprising a photopolymerizable moiety and a glycosaminoglycan component comprising a photopolymerizable moiety.

30. The system of claim 29, wherein the photopolymerizable synthetic polymer is a poly(ethylene glycol), and wherein the photopolymerizable moiety is an acrylate, a diacrylate, an oligoacrylate, a dimethacrylate, or an oligomethoacrylate.

31. The system of claim 29, wherein the glycosaminoglycan component comprises chondroitin-4-sulfate and chondroitin-6-sulfate.

32. The system of claim 29, wherein the musculoskeletal tissue is an intervertebral disc tissue, cartilage, bone, muscle, or tendon.

33. A method of producing cartilage, the method comprising maintaining a multi-layer cell composition of claim 1 under conditions such that at least a portion of the MSC in the cell composition differentiate into chondrocytes, and wherein the chondrocytes synthesize cartilage components.

34. The method of claim 33, wherein the cartilage components comprise aggrecan and type II collagen.

35. The method of claim 33, wherein said maintaining is carried out in vitro.

36. The method of claim 35, wherein said maintaining is carried out for a period of time of from about 48 hours to about 3 weeks.

37. The method of claim 33, further comprising preparing a cartilage production composition comprising said multi-layer composition, and introducing said cartilage production composition into a treatment site in an individual.

38. The method of claim 37, wherein the treatment site is a diarthroidal joint.

39. The method of claim 37, wherein the treatment site is an intervertebral disc.

40. The method of claim 33, wherein said cartilage production composition comprises a photopolymerizable scaffold component, and wherein said method further comprises exposing the introduced cartilage production composition to ultraviolet light.

41. A method of producing a musculoskeletal tissue, the method comprising maintaining the multi-layer cell composition of claim 1 under conditions such that at least a portion of the MSC in the cell composition differentiates into musculoskeletal tissue-type cells.

42. The method of claim 41, wherein the musculoskeletal tissue is an intervertebral disc tissue, cartilage, bone, muscle, or tendon.

43. The method of claim 41, wherein said maintaining is carried out in vitro.

44. The method of claim 43, wherein said maintaining is carried out for a period of time of from about 48 hours to about 3 weeks.

45. The method of claim 41, further comprising preparing a musculoskeletal tissue production composition comprising said multi-layer composition, and introducing said musculoskeletal tissue production composition into a treatment site in an individual.

46. The method of claim 45, wherein the treatment site is an intervertebral disc.

47. A method of making the multi-layer cell composition of claim 1, the method comprising:
a) forming a pellet of the second layer cells in a liquid medium in a tube having an inner surface that is substantially non-adherent for the cells; and
b) adding the first layer of cells to the pellet,
wherein the pellet becomes suspended in the liquid medium, and wherein the first layer cells adhere to and surround the pellet.

* * * * *

UNITED STATES PATENT AND TRADEMARK OFFICE
CERTIFICATE OF CORRECTION

| | | |
|---|---|---|
| PATENT NO. | : 8,603,819 B2 | Page 1 of 1 |
| APPLICATION NO. | : 12/993668 | |
| DATED | : December 10, 2013 | |
| INVENTOR(S) | : Allon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 326 days.

Signed and Sealed this
Fourteenth Day of April, 2015

Michelle K. Lee
*Director of the United States Patent and Trademark Office*